(12) United States Patent
Buffiere et al.

(10) Patent No.: US 12,163,967 B2
(45) Date of Patent: Dec. 10, 2024

(54) BLOOD ANALYSIS SYSTEMS AND METHODS

(71) Applicants: BIO-RAD LABORATORIES, INC., Hercules, CA (US); BIO-RAD EUROPE GMBH, Basel (CH)

(72) Inventors: Frederic Buffiere, Marnes la Coquette (FR); Sylvie Villard-Saussine, Marnes la Coquette (FR); Eliane Rivalin, Marnes la Coquette (FR); Laurent Guillon, Marnes la Coquette (FR); Johann Guegan, Marnes la Coquette (FR)

(73) Assignee: BIO-RAD EUROPE GMBH, Basel (CH)

( * ) Notice: Subject to any disclaimer, the term of this patent is extended or adjusted under 35 U.S.C. 154(b) by 981 days.

(21) Appl. No.: 16/945,960

(22) Filed: Aug. 3, 2020

(65) Prior Publication Data

US 2020/0363434 A1 Nov. 19, 2020

Related U.S. Application Data

(62) Division of application No. 15/543,579, filed as application No. PCT/IB2016/050157 on Jan. 14, 2016, now Pat. No. 10,732,189.

(30) Foreign Application Priority Data

Jan. 14, 2015 (EP) ..................................... 15151176

(51) Int. Cl.
*G01N 33/80* (2006.01)
*B01L 3/00* (2006.01)
(Continued)

(52) U.S. Cl.
CPC ........ *G01N 33/80* (2013.01); *B01L 3/502761* (2013.01); *B01L 3/502776* (2013.01);
(Continued)

(58) Field of Classification Search
CPC ............. G01N 33/54306; G01N 33/80; G01N 33/56966; B01L 2300/0864
See application file for complete search history.

(56) References Cited

U.S. PATENT DOCUMENTS 5,773,222 A 6/1998 Scott
6,326,058 B1 12/2001 Biebuyck et al.
(Continued)

FOREIGN PATENT DOCUMENTS

CN 1438486 8/2003
EP 0 223 978 8/1992
(Continued)

OTHER PUBLICATIONS

Ainla et al. Hydrodynamic Flow Confinement Technology in Microfluidic Perfusion Devices. Micromachines 3: 442-461 (2012).*
(Continued)

*Primary Examiner* — Gailene Gabel
(74) *Attorney, Agent, or Firm* — SALIWANCHIK, LLOYD & EISENSCHENK

(57) ABSTRACT

Blood typing systems and methods are provided. In one embodiment, the method may be achieved by applying a sample to a surface of a substrate having one or more binding agents immobilized thereon, wherein the one or more binding agents are capable of binding to one or more substances in the sample; substantially removing unbound material from at least a portion of the substrate having immobilized binding agent; and detecting substances bound to the one or more binding agents immobilized on the substrate; wherein the applying the sample to the surface of
(Continued)

the substrate step is concurrent with the removing unbound material from at least a portion of the substrate step. Systems and other methods are also described and illustrated.

6 Claims, 13 Drawing Sheets

(51) Int. Cl.
    *G01N 33/543*     (2006.01)
    *G01N 33/569*     (2006.01)

(52) U.S. Cl.
    CPC ...... *B01L 3/5085* (2013.01); *G01N 33/54306* (2013.01); *G01N 33/54373* (2013.01); *G01N 33/56966* (2013.01); *B01L 3/502715* (2013.01); *B01L 3/502753* (2013.01); *B01L 2200/0652* (2013.01); *B01L 2300/024* (2013.01); *B01L 2300/027* (2013.01); *B01L 2300/0636* (2013.01); *B01L 2300/0822* (2013.01); *B01L 2300/0829* (2013.01); *B01L 2300/0864* (2013.01); *B01L 2300/0883* (2013.01); *B01L 2300/089* (2013.01); *B01L 2300/0896* (2013.01); *B01L 2300/163* (2013.01); *B01L 2400/0406* (2013.01)

(56) References Cited

U.S. PATENT DOCUMENTS

| | | | |
|---|---|---|---|
| 6,656,745 | B1 | 12/2003 | Cole |
| 7,329,111 | B2 | 2/2008 | Delamarche et al. |
| 7,371,684 | B2 | 5/2008 | Colburn et al. |
| 7,491,272 | B2 | 2/2009 | Delamarche et al. |
| 7,618,792 | B2 | 11/2009 | Banerjee |
| 7,695,687 | B2 | 4/2010 | Delamarche et al. |
| 7,740,472 | B2 | 6/2010 | Delamarche et al. |
| 7,855,101 | B2 | 12/2010 | Furman et al. |
| 7,947,907 | B2 | 5/2011 | Colburn et al. |
| 7,980,446 | B2 | 7/2011 | Buchwalter et al. |
| 7,982,312 | B2 | 7/2011 | Colburn et al. |
| 7,992,591 | B2 | 8/2011 | Delamarche |
| 8,020,586 | B2 | 9/2011 | Delamarche |
| 8,030,006 | B2 | 10/2011 | Robb et al. |
| 8,051,878 | B2 | 11/2011 | Delamarche |
| 8,206,025 | B2 | 6/2012 | Natarajan |
| 8,491,083 | B2 | 7/2013 | Boday et al. |
| 8,517,596 | B2 | 8/2013 | Natarajan |
| 8,546,084 | B2 | 10/2013 | Chaibi |
| 8,551,859 | B2 | 10/2013 | Ackerson et al. |
| 8,580,530 | B2 | 11/2013 | Buffiere et al. |
| 8,585,280 | B2 | 11/2013 | Natarajan |
| 8,674,474 | B2 | 3/2014 | Ackerson et al. |
| 8,680,023 | B2 | 3/2014 | Coyer et al. |
| 8,680,024 | B2 | 3/2014 | Coyer et al. |
| 8,695,639 | B2 | 4/2014 | Delamarche et al. |
| 8,695,641 | B2 | 4/2014 | Delamarche et al. |
| 8,748,355 | B2 | 6/2014 | Campbell et al. |
| 9,745,949 | B2 | 8/2017 | Delamarche et al. |
| 10,732,189 | B2 | 8/2020 | Buffiere et al. |
| 2005/0069462 | A1 | 3/2005 | Humenik et al. |
| 2005/0069949 | A1 | 3/2005 | Humenik et al. |
| 2005/0247673 | A1 | 11/2005 | Delamarche et al. |
| 2009/0318302 | A1 | 12/2009 | Delamarche et al. |
| 2009/0318303 | A1 | 12/2009 | Delamarche et al. |
| 2010/0176089 | A1 | 7/2010 | Delamarche et al. |
| 2010/0184102 | A1* | 7/2010 | Chaibi ............ G01N 33/80 435/7.25 |
| 2010/0256005 | A1 | 10/2010 | Petrik et al. |
| 2011/0076698 | A1 | 3/2011 | Wang et al. |
| 2011/0117539 | A1 | 5/2011 | Delamarche et al. |
| 2012/0034677 | A1 | 2/2012 | Delamarche et al. |
| 2012/0214153 | A1 | 8/2012 | Delamarche et al. |
| 2012/0283133 | A1 | 11/2012 | Delamarche et al. |
| 2013/0098481 | A1 | 4/2013 | Delamarche et al. |
| 2013/0121893 | A1 | 5/2013 | Delamarche et al. |
| 2013/0333761 | A1 | 12/2013 | Delamarche et al. |
| 2013/0337578 | A1 | 12/2013 | Delamarche et al. |
| 2014/0004264 | A1 | 1/2014 | Duerig et al. |
| 2014/0072777 | A1 | 3/2014 | Boday et al. |
| 2014/0090715 | A1 | 4/2014 | Delamarche et al. |
| 2014/0137962 | A1 | 5/2014 | Delamarche et al. |
| 2015/0140579 | A1 | 5/2015 | Chaibi |
| 2015/0253251 | A1* | 9/2015 | McKee ............ G01N 33/54366 422/69 |

FOREIGN PATENT DOCUMENTS

| | | |
|---|---|---|
| JP | 2010-071828 | 4/2010 |
| JP | 2011-522228 | 7/2011 |
| JP | 2013-543971 | 12/2013 |

OTHER PUBLICATIONS

Kaigala et al. Microfluidics in the Open Space for Performing Localized Chemistry on Biological Interfaces. Angew. Chem. Int. Ed. 51: 11224-11240 (2012).*

Autebert, J. et al. "Hierarchical Hydrodynamic Flow Confinement: Efficient Use and Retrieval of Chemicals for Microscale Chemistry on Surfaces" *Langmuir*, Mar. 13, 2014, pp. 3640-3645, vol. 30, No. 12.

Written Opinion in International Application No. PCT/IB2016/050157, Mar. 8, 2016, pp. 1-9.

* cited by examiner

Plasma A+  Plasma O+  Plasma O+
60 seconds  30 seconds  60 seconds

BLOOD ANALYSIS SYSTEMS AND METHODS

CROSS-REFERENCE TO RELATED APPLICATIONS

This application is a divisional of U.S. Ser. No. 15/543,579, filed Jul. 14, 2017, now U.S. Pat. No. 10,732,189, which is the U.S. national stage application of International Patent Application No. PCT/IB2016/050157, filed Jan. 14, 2016, which claims the benefit of U.S. Provisional Patent Application No. 62/107,114, filed Jan. 23, 2015.

FIELD

This disclosure relates generally to analysis of patient samples such as blood samples.

BACKGROUND

Millions of people donate their blood each year. Before the blood from the donor can be transfused into a recipient, the blood must be typed. Typically, the blood is tested for ABO and RH1 (Rhesus D antigen) blood groups and is screened for alloimmune antibodies of clinical significance. To determine the blood group, red blood cells (RBCs or erythrocytes) are reacted separately with anti-A, anti-B, anti-AB and anti-D antibodies. This type of test is known as antigen typing (e.g., grouping and phenotyping). The serum/plasma from the same blood sample is also individually tested with Type A and Type B reagent RBCs and at least two different Type O reagent cells representing most of the antigens of clinical significance. The type of test with Type A and Type B reagent RBCs is known as reverse typing and the type of test with Type O reagent cells is known as antibody screening.

More than 150 million tests are performed annually in blood centers to determine the blood groups as well as antibodies of clinical significance in the serum/plasma. Generally, transfusion of blood is required in emergency situations for which it is desirable to determine the compatibility between the donor and recipient in as short a time as possible. An automated high-throughput system and method of blood typing is therefore desired that can test multiple samples at once and that can provide quick test results. Additionally, needing less blood sample from the patient is also desirable.

SUMMARY

In an embodiment, a method is disclosed in which the presence or absence of a substance in a sample is determined. The method comprises applying a sample to a surface of a substrate having a binding agent immobilized thereon, wherein the binding agent is capable of binding to a substance in the sample; removing unbound material from at least a portion of the substrate having immobilized binding agent; and responsive to detecting the substance bound to the binding agent immobilized on the substrate, identifying the substance present in the sample; and responsive to not detecting the substance bound to the binding agent immobilized on the substrate, determining that the substance is absent in the sample; wherein the applying the sample to the surface of the substrate step is concurrent with the removing unbound material from at least a portion of the substrate step. The applying a sample to the surface of the substrate and the removing unbound material from at least a portion of the substrate steps may be performed with a hydrodynamic flow confinement dispenser. In an embodiment, the hydrodynamic flow confinement dispenser is a microfluidic probe. In an embodiment, the hydrodynamic flow confinement dispenser is a microfluidic probe having multiple microchannels. In another embodiment, the hydrodynamic flow confinement dispenser is an array of microfluidic probes.

In some embodiments, a system for determining the presence or absence of a substance in a sample includes a substrate having a binding agent immobilized in a discreet location, wherein the binding agents are capable of binding to a substance in a sample; a dispenser configured to concurrently dispense a sample onto the substrate and to remove unbound material from the substrate; a light source configured to illuminate the substrate; and a detector configured to detect the presence or absence of the substance bound to the binding agent.

Further disclosed herein are blood analysis systems and methods of using these systems to analyze blood samples. More particularly, the disclosure relates to systems and methods for detection of erythrocyte group and phenotype (antigen typing), for screening and identification of typical anti-erythrocyte antibodies reverse typing and atypical anti-erythrocyte antibodies (antibody screening), for the determination of the compatibility between a donor and a recipient (cross-matching) and for the demonstration of erythrocytes coated with antibodies and/or with activated serum complement fractions (e.g., Direct Antiglobulin Test).

In some embodiments, the hydrodynamic flow confinement dispenser includes structures for separation of plasma from red blood cells in a whole blood sample. In an embodiment for separating red blood cells from plasma, the microchannel has a diameter of less than 6 micrometers. In some embodiments, the diameter is less than 4 micrometers or less than 2 micrometers or 1-2 micrometers. The cross section of the microchannel may be any appropriate shape including rectangle, square, circular, oval and elliptical or a combination of those.

In some embodiments, the surface of the substrate is wet. In an embodiment, the applying a sample to the surface of the substrate step comprises dispensing one or more samples each in at least one discreet path. In certain embodiments, the path is a straight line. In some embodiments, the path is from about 25 nanometers to about 500 micrometers wide. In an embodiment, the applying a sample to the surface of the substrate step comprises dispensing one or more samples each in at least one discreet spot. In some embodiments, the at least one discreet spot is from about 25 nanometers to about 500 micrometers in diameter. In some embodiments, the sample is selected from a group consisting of whole blood, red blood cells, plasma, serum and saliva.

In an embodiment, the one or more binding agents comprise one or more antibodies, or fragments thereof, or some specific lectins, to red blood cell antigens and the substance in the sample detected is the red blood cell antigens.

In another embodiment, the one or more binding agents comprise one or more native or hemolyzed phenotyped red blood cells, chemically synthesized polypeptide and polysaccharide blood group antigens, recombinant red blood cell antigens or red blood cell membrane extracts and the substance is one or more antibodies, or fragments thereof, to the red blood cell antigens, the recombinant red blood cell antigens or red blood cell membrane extracts.

In yet another embodiment, the binding agent is a multipart binding agent. The first portion deposited on the substrate comprises lectins or one or more antibodies, or fragments thereof, to red blood cell antigens. The antibodies are universal antibodies to red blood cells. The second part of the binding agent deposited on the substrate are phenotyped or non-phenotyped red blood cells from a potential blood donor and are bound to the binding agent. The substance is plasma from a patient in need of a blood transfusion and antibodies, or fragments thereof in the patient plasma bind to the red blood cells from the donor.

In yet another embodiment, the one or more binding agents comprise one or more antibodies, or fragments thereof, to human immunoglobulins and/or activated serum complement fractions and the substance is red blood cells coated with antibodies and/or with activated serum complement fractions.

In some embodiments, the one or more binding agents are immobilized in discreet lines. In some embodiments, the one or more binding agents are immobilized in discreet spots. In some embodiments, 1-100 binding agents are bound to the surface of the substrate.

A system for antibody screening, antigen typing (including Direct Antiglobulin Test) and cross-matching, the system comprising a substrate having a binding agent immobilized in discreet locations, wherein the binding agent is capable of binding to a substance in a sample; a dispenser configured to simultaneously dispense the sample onto the substrate and to remove unbound material from the substrate; a light source configured to illuminate the substrate; and a detector configured to detect the presence or absence of the substance bound to the binding agent.

In some embodiments, a system for cross-matching includes a substrate having donor red blood cells immobilized in discreet locations thereon; a dispenser configured to dispense donor red blood cells and/or patient plasma onto the substrate and to simultaneously remove unbound donor red blood cells or an unbound portion of the patient plasma from the substrate; a light source configured to illuminate the substrate; and a detector configured to detect the presence or absence of antibodies bound to the donor red blood cells.

Item 1. A method of determining the presence or absence of a substance in a sample, the method comprising:
  applying the sample to a surface of a substrate having a binding agent immobilized thereon, wherein the binding agent is capable of binding to the substance in the sample;
  removing unbound material from at least a portion of the substrate having immobilized binding agent; and
  responsive to detecting the substance bound to the binding agent immobilized on the substrate, identifying the substance present in the sample;
  and responsive to not detecting the substance bound to the binding agent immobilized on the substrate, determining that the substance is absent in the sample;
  wherein the applying the sample to the surface of the substrate step is concurrent with the removing unbound material from at least a portion of the substrate step.

Item 2. The method of Item 1, wherein the applying the sample to the surface of the substrate and the removing unbound material from at least a portion of the substrate steps are performed with a hydrodynamic flow confinement dispenser.

Item 3. The method of Item 2, wherein the dispenser is a microfluidic probe.

Item 4. The method of Item 3, wherein the dispenser is a microfluidic probe having a plurality of microchannels.

Item 5. The method of Item 3 or 4, wherein the dispenser is an array of microfluidic probes.

Item 6. The method of any one of previous Items 3 to 5, wherein the dispenser is a microfluidic probe having a microchannel that excludes red blood cells based on size.

Item 7. The method of Item 6, wherein the microchannel includes a cross section having a diameter of less than 6 micrometers.

Item 8. The method of Item 6, wherein the microchannel includes a cross section having a diameter of less than 4 micrometers.

Item 9. The method of Item 6, wherein the microchannel includes a cross section having a diameter of less than 2 micrometers.

Item 10. The method of Item 6, wherein a diameter of the microchannel includes a cross section having a diameter of 1-2 micrometers.

Item 11. The method of any one of previous Items 1 to 10, wherein the surface of the substrate is wet.

Item 12. The method of any one of previous Items 1 to 11, wherein the applying a sample to the surface of the substrate step comprises dispensing one or more samples each in at least one discreet path.

Item 13. The method of Item 12, wherein the path is a straight line.

Item 14. The method of Item 12 or 13, wherein the path is from between 25 nanometers to 500 micrometers wide.

Item 15. The method of any one of previous Items 1 to 14, wherein the applying a sample to the surface of the substrate step comprises dispensing one or more samples each in at least one discreet spot.

Item 16. The method of any one of previous Items 1 to 15, wherein the sample comprises a blood sample.

Item 17. The method of any one of previous Items 1 to 16, wherein the sample comprises a component selected from the group consisting of whole blood, red blood cells, plasma and serum.

Item 18. The method of any one of previous Items 1 to 17, wherein the binding agent comprises one or more antibodies to red blood cell antigens.

Item 19. The method of any one of previous Items 1 to 18, wherein the binding agent comprises one or more native or hemolyzed phenotyped red blood cells.

Item 20. The method of any one of previous Items 1 to 19, wherein the binding agent comprises one or more recombinant antigens.

Item 21. The method of any one of previous Items 1 to 20, wherein the binding agent comprises one or more antibodies to red blood cell antigens and one or more native or hemolyzed phenotyped red blood cells.

Item 22. The method of any one of previous Items 1 to 21, wherein the binding agent is immobilized in a discreet line.

Item 23. The method of any one of previous Items 1 to 21, wherein the binding agent is immobilized in a discreet spot.

Item 24. The method of any one of previous Items 1 to 23, wherein the binding agent is 1-50 binding agents.

Item 25. The method of any one of previous Items 1 to 24, wherein the substance comprises one or more antibodies to red blood cell antigens.

Item 26. The method of any one of previous Items 1 to 25, wherein the substance comprises one or more red blood cell antigens.

Item 27. The method of any one of previous Items 1 to 26, wherein the substrate is formed of at least one material selected from a group consisting of polyethylene terephthalate, polypropylene, polystyrene, dextran polymer, dendrimer, oligonucleotide, polycarbonate, plastic, glass, silicon, silicon oxide, metals and metal oxides, and polymer functionalized metals and metal oxides, PVDF, nitrocellulose, nylon and polysulfone.

Item 28. A system comprising:
a substrate having a binding agent immobilized in discreet locations, wherein the binding agent is capable of binding to a substance in a sample;
a dispenser configured to simultaneously dispense the sample onto the substrate and to remove unbound material from the substrate; and
a detector configured to detect the presence or absence of the substance bound to the binding agent.

Item 29. The system of Item 28, wherein the dispenser is a microfluidic probe.

Item 30. The system of Item 28, wherein the dispenser is an array of microfluidic probes.

Item 31. The method of Item 28, wherein the dispenser is a microfluidic probe having a plurality of microchannels.

Item 32. The system of any one of previous Items 28 to 31, wherein the dispenser is a microfluidic probe having a microchannel that excludes red blood cells based on size.

Item 33. The system of Item 32, wherein the microchannel includes a cross section having a diameter of less than 6 micrometers.

Item 34. The system of Item 32, wherein the microchannel includes a cross section having a diameter of less than 4 micrometers.

Item 35. The system of Item 32, wherein the microchannel includes a cross section having a diameter of less than 2 micrometers.

Item 36. The system of Item 32, wherein a diameter of the microchannel includes a cross section having a diameter of less than 1-2 micrometers.

Item 37. The system of any one of previous Items 28 to 36, wherein the substrate is formed of at least one material selected from a group consisting of polyethylene terephthalate, polypropylene, polystyrene, dextran polymer, dendrimer, oligonucleotide, polycarbonate, plastic, glass, silicon, silicon oxide, metals and metal oxides, and polymer functionalized metals and metal oxides, PVDF, nitrocellulose, nylon and polysulfone.

Item 38. A method of cross-matching comprising:
applying donor red blood cells to a surface of a substrate having a binding agent immobilized thereon, wherein the binding agent is capable of binding to the donor red blood cells;
removing unbound donor red blood cells from at least a portion of the substrate having immobilized binding agent; wherein the applying the donor red blood cells to the surface of the substrate step is concurrent with the removing unbound donor red blood cells from at least a portion of the substrate step;
depositing patient plasma on top of the donor red blood cells;
removing an unbound portion of the patient plasma; wherein the depositing a patient plasma step is concurrent with the removing unbound portion of the patient plasma step;
responsive to detecting an antibody bound to the donor red blood cells, determining that the antibody is present in the patient plasma; and
responsive to not detecting the antibody bound to the donor red blood cells, determining that the antibody is absent in the patient plasma.

Item 39. The method of Item 38, wherein the applying donor red blood cells, removing unbound donor red blood cells, depositing patient plasma and removing the unbound portion of patient plasma steps are performed with a microfluidic probe.

Item 40. The method of Item 38 or 39, wherein the donor red blood cells are native or hemolyzed phenotyped red blood cells.

Item 41. The method of any one of previous Items 38 to 40, wherein the binding agent comprises bound lectins or universal anti-red blood cell antibodies.

Item 42. A system for crossmatching comprising:
a substrate having donor red blood cells immobilized in discreet locations thereon;
a dispenser configured to simultaneously dispense donor red blood cells or patient plasma onto the substrate and to remove unbound donor RBCs or an unbound portion of the patient plasma from the substrate; and
a detector configured to detect the presence or absence of antibodies bound to the donor red blood cells.

BRIEF DESCRIPTION OF THE DRAWINGS

FIG. 13B is a close up view of one of the spots shown in FIG. 13A.

FIG. 18A is an image of fluorescent spots on a cross-matching slide and FIG. 18B is the measured fluorescence intensity of each spot.

DETAILED DESCRIPTION

Overview

Figure 1:
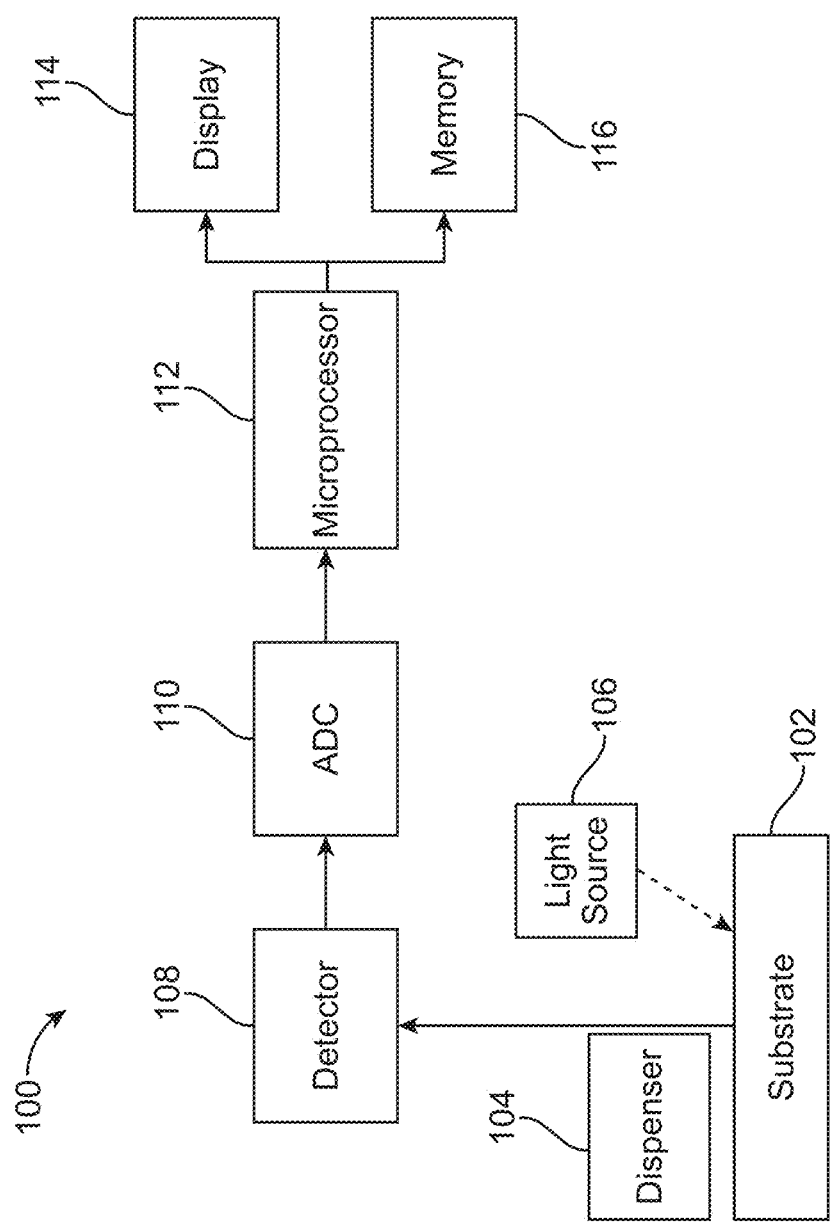
FIG. 1 shows a schematic view of a blood analysis system according to an embodiment of the invention.

Among all the antigenic variants of an erythrocyte membrane antigen constituting the blood groups, more than thirty erythrocyte antigen systems have been identified to date in humans: the ABO system with the antigens A, B and H, the Rhesus (RH) system with in particular the antigens D (the absence of the D antigen being noted d), C, E, c and e, the Kell (KEL) system with in particular the two antigens K and k, the Duffy (FY) system with in particular the antigens $Fy^a$ and $Fy^b$, the Kidd (JK) system with in particular the antigens $Jk^a$ and $Jk^b$, or alternatively other systems that are less commonly investigated in practice, such as the MNS system, the Lewis (LE) system, etc.

The standard transfusion generally takes into account the groups in the ABO system and the Rhesus D system (D+ ord). However, in situations where there is a risk of an atypical agglutinin appearing, a certain number of other antigens of the Rhesus system systems are taken into account, in particular C, c, E and e antigens and Kell, or even other systems.

Antibodies directed against erythrocyte antigens. Outside of pathological situations, such as in the case of autoimmune diseases, the serum of an individual may contain two types of antibodies directed against erythrocyte antigens:

(i) Antibodies referred to as typical (or regular) and directed against the antigens of the ABO system (for example, anti-A antibody in an individual of group B).

(ii) Antibodies referred to as atypical (or immune), the presence of which in the serum or plasma is circumstantial, and which are directed more particularly against non-ABO system antigens.

The "typical" or "regular" antibodies are more frequently immunoglobulins of M and/or A isotype which are capable of agglutinating red blood cells in vitro. The "atypical", or "irregular", or "immune", antibodies are most commonly of G isotype, appearing when there is antigenic stimulation by foreign red blood cells, for example following immunization against one or more antigens during a blood transfusion or else during a pregnancy due to a maternal immunoreaction directed against the fetal erythrocyte antigens that do not belong to the maternal blood group, in particular at the time of the birth.

Various testing used in analyzing blood includes:

ABO grouping: This analysis is the result of the combination and the interpretation of two types of analyses: serum analyses with plasma or serum and cell analyses using the blood cell pellet (respectively a reverse and forward grouping).

In the forward grouping, the individual's red blood cells are brought into contact with test antibodies, each having precise antibody specificity, directed against an antigen of the ABO system (anti-A, anti-B and anti-AB antibodies).

In the reverse grouping, the individual's serum or plasma, containing typical circulating antibodies, is brought into contact with phenotyped red blood cells, each belonging to a precise antigenic group of the ABO system.

Phenotyping assay: The techniques normally used for phenotyping consist, in general, in screening for the presence or absence of the antigen being at the surface of red blood cell investigated, using specific antibodies.

Screening and/or identification of atypical anti-erythrocyte antibodies: This test is used to detect the presence or absence, in an individual's blood, of antibodies directed against various erythrocyte antigens. For this, it is sought to demonstrate the binding of these antibodies (IgG and/or IgM) to phenotyped red blood cells, the antigens of which are known or/and to recombinant blood group antigens. When bound on phenotyped red blood cells or recombinant antigens, these atypical anti-erythrocyte antibodies are revealed by an anti-immunoglobulin antibody. In a first step, use is made of a panel of "screening" red blood cells (two or three red blood cells chosen so as to comprise all the antigens of importance in transfusion for detecting (but not identifying) the presence or absence of atypical antibodies). When the screening is positive, the specificity of the atypical antibody or antibodies present is then identified by means of at least one panel of "identifying" red blood cells, in general comprising 10 to 15, or even 20, different red blood cells phenotyped in the vast majority of the known blood group systems.

Cross-matching assay: The objective of this analysis is to predict donor-recipient compatibility prior to infusing a recipient with a donor's blood. This is used to confirm compatibility beyond the basic typing that is done of a donor's blood. The red blood cells originating from potential donor are brought together with the potential transfused recipient's serum/plasma. If the potential recipient sample contains antibodies against the potential donor's red blood cells, they are revealed with an anti-immunoglobulin antibody. Such an analysis results only in the determination of the presence or absence of an antibody, and does not make it possible to determine the specificity thereof. In another type of cross-matching called "minor" cross-matching, the plasma originating from the potential donor is brought together with the potential transfused recipient's red blood cells. If the potential donor sample contains antibodies against the potential recipient's red blood cells, the antibodies are revealed with an anti-immunoglobulin antibody.

Direct Antiglobulin Test: In particular newborns or patients suffering from haemolytic anaemia or autoimmune diseases for example, the red blood cells are sensitized in vivo by antibodies or/and by serum complement fractions. These antibodies or activated serum complement fractions present at the surface of erythrocytes sensitized in vivo are themselves capable of constituting antigens carried by erythrocytes and are directly detected by an anti-immunoglobulin antibody and/or an anti-complement antibody.

Described herein are systems and methods for blood analysis including the testing described above. The systems and methods facilitate the automation of blood analysis. The systems and methods can be used for detection of grouping and phenotyping, for screening and/or identification of antibodies, cross-matching and direct antiglobulin test.

Advantages of the systems and methods described herein include, but are not limited to: (1) providing systems that are compact in size that deliver nanoliter to microliter volumes of reagents and patient samples; (2) providing systems that localize the reaction chemistry and decrease reaction time; (3) providing systems capable of performing multiplex assays (e.g., testing sample from multiple patients and/or testing a single sample for multiple analytes); (4) providing systems capable of simultaneous phenotyping (e.g., forward blood typing) and antibody screening/identification (e.g., reverse blood typing); (5) providing systems capable of depositing native or hemolyzed red blood cells onto a substrate while maintaining the antigenicity of the native or hemolyzed red blood cells; (6) providing systems capable of cross-matching red blood cells that may be transfused into a patient and/or (7) providing systems in which the application of sample and washing of unbound material steps may be performed simultaneously which in turn decreases assay time.

As used in this specification and the appended claims, the singular forms "a", "an", and "the" include plural referents unless the content clearly dictates otherwise. Thus, for example, reference to a system comprising "a binding agent" includes system comprising one or more binding agents. Likewise, reference to "a substance" includes one or more substances. As used herein, the term "about" refers to the recited number and any value within 10% of the recited number. Thus, "about 25" refers to any value between 22.5 and 27.5, including 22.5 and 27.5.

Systems

Referring to FIG. 1, a system 100 for analyzing blood is illustrated. In an embodiment, the system 100 is used to phenotype (also known as antigen typing), to antibody screen and identify or to cross-match of patient plasma with donor red blood cells. The system 100 includes a substrate 102, a dispenser 104 (e.g., a microfluidic probe), a light source 106 and a detector 108.

The substrate 102 provides a surface onto which a binding agent 110 (shown in FIG. 2) is immobilized or bound. The substrate 102 is generally planar in shape and may be formed of one or more materials including, but not limited to, polyethylene terephthalate (e.g., Mylar), polypropylene, polystyrene, polycarbonate, plastic, glass, silicon, silicon oxide, and/or metals and metal oxides either bare or functionalized with polymer or activated groups such as carboxyl, amine, tosyl and others. In some embodiments, the substrate is a slide formed of one or more materials including, but not limited to, polyethylene terephthalate (e.g., Mylar), polypropylene, polystyrene, polycarbonate, plastic, glass, silicon, silicon oxide, and/or metals and metal oxides either bare or functionalized with polymers. The substrate 102 may contain microwells or nanowells. Examples of polymers with which to functionalize the surface of substrates formed from metal or metal ozide include glycidoxypropyltriethoxysilane, poly-L-lysine, polybrene, polyethylene glycol polymers, dextran polymer, aminopropylsilane, caroxysilane, hydrogels and polymer brushes, and/or self-assembled monolayers of e.g. functionalized alkyl thiols, dendrimers or oligonucleotides. In an embodiment, the substrate 102 is coated with gold. In an embodiment, the substrate 102 is a microtiter plate having a plurality of wells in which the binding agents may be immobilized. In some embodiments, the substrate 102 is a membrane formed of material including, for example, nitrocellulose, polyvinylidene fluoride, nylon or polysulfone.

The surface of the substrate 102 may be wet. A wet surface is desirable in some embodiments in which the binding agents require hydration to remain active. Exemplary fluids used to wet the surface of the substrate 102 include, but are not limited to, buffer, water, saline and/or oil (e.g., mineral oil).

In some embodiments, the substrate 102 is mounted on a platform that is moveable in the X-Y- and/or Z direction.

Figure 3:
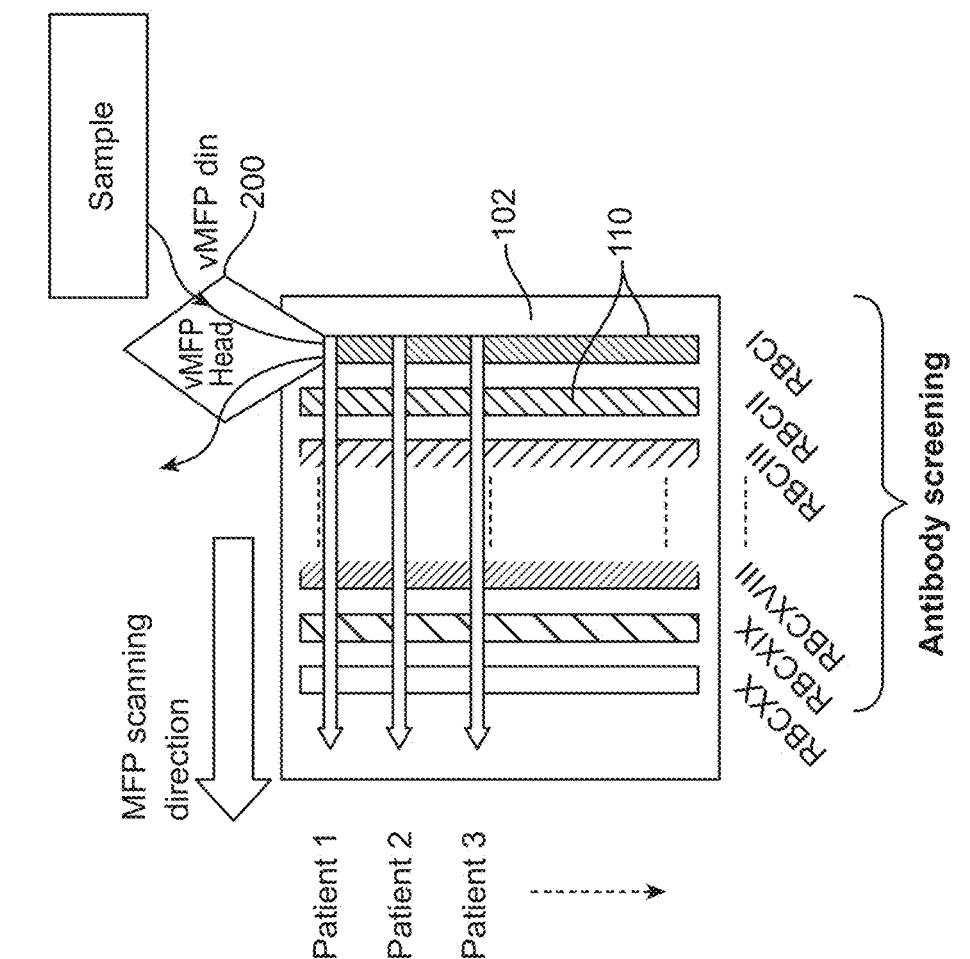
FIG. 3 shows a top view of a substrate having an array of binding agents applied thereon in which a sample (e.g., plasma having antibodies) is applied with a microfluidic probe according to another embodiment of the invention. The embodiment may be used for antibody screening and/or identification and the binding agents are native or hemolyzed phenotyped RBCs or recombinant blood group antigens.
Figure 2:
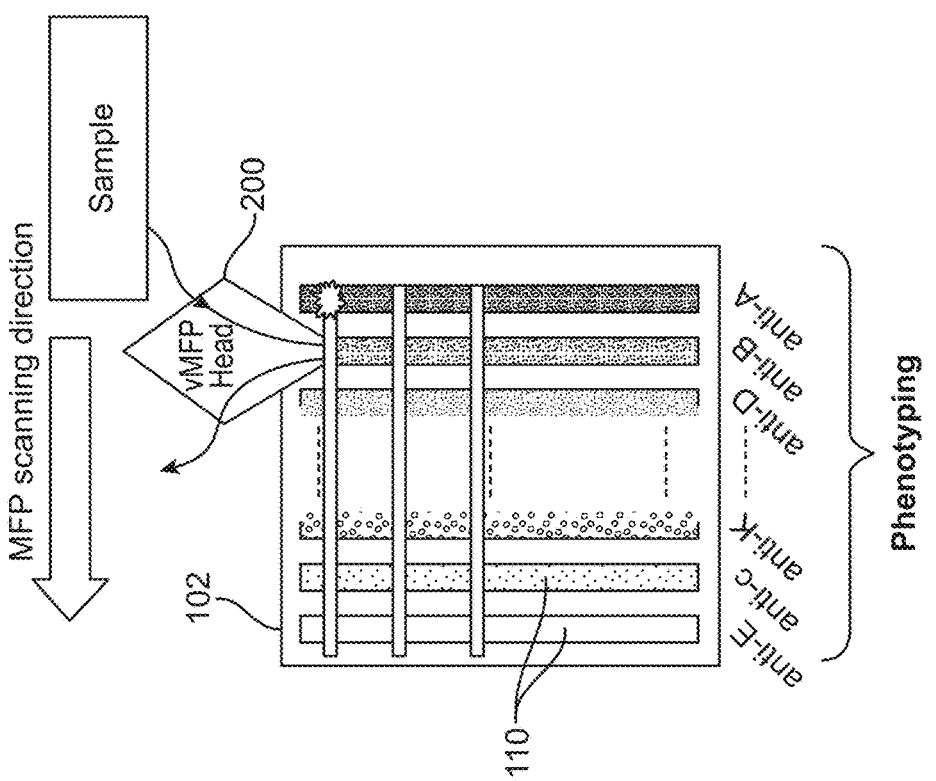
FIG. 2 shows a top view of a substrate having an array of binding agents applied thereon in which a sample (e.g., RBCs) is applied with a microfluidic probe according to an embodiment of the invention. The embodiment may be used for antigen typing and the binding agents are antibodies to RBCs.
Figure 4:
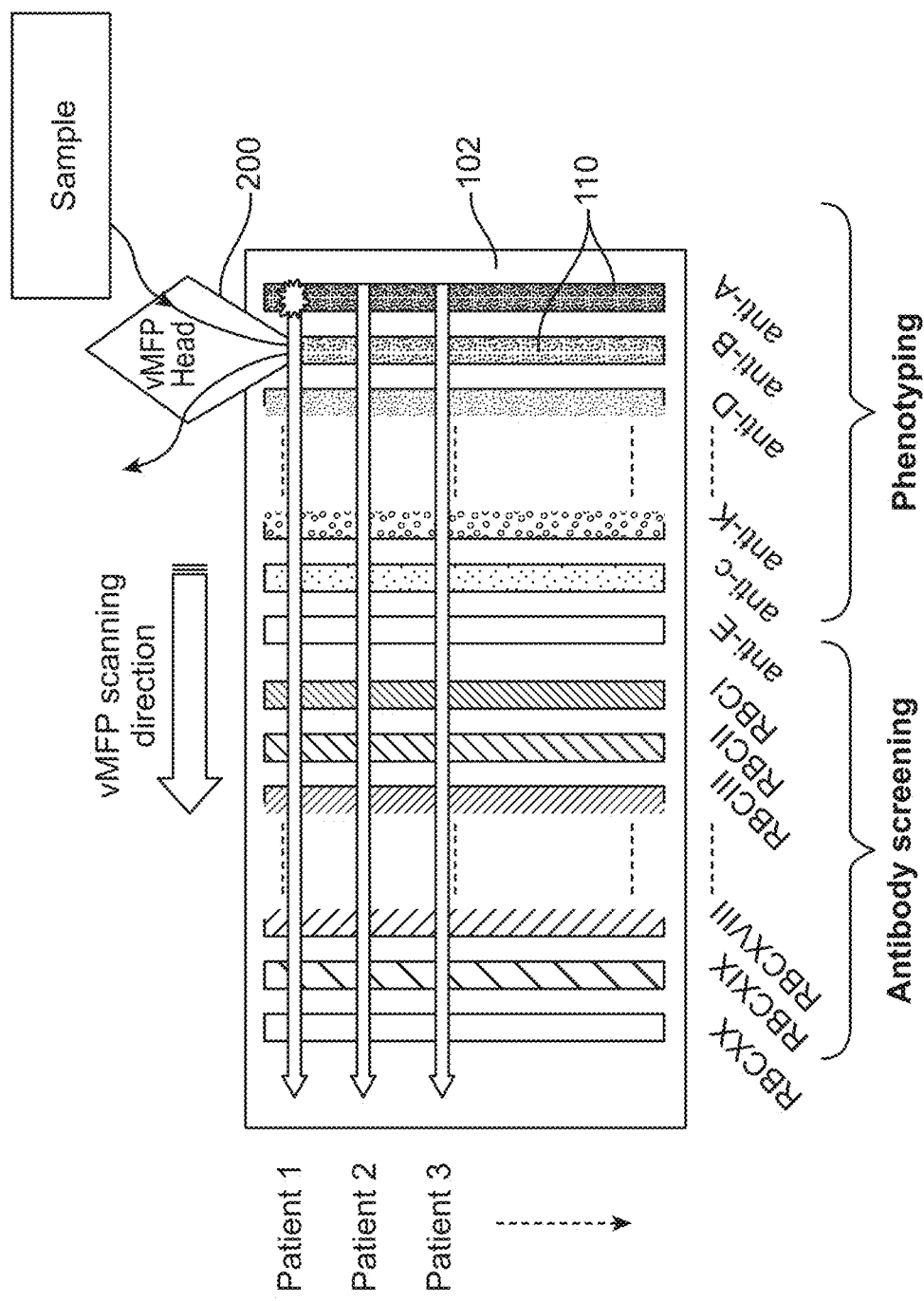
FIG. 4 shows a top view of a substrate having an array of binding agents applied thereon in which a sample (e.g., RBCs and/or plasma having antibodies) is applied with a microfluidic probe according to another embodiment of the invention. The embodiment may be used for both antigen typing and antibody screening and/or identification.

In embodiments illustrated in FIGS. 2-4, one or more binding agents 110 are bound to a surface of the substrate 102 in an array of lines. In an embodiment, the lines are about 25 nanometers to about 500 micrometers wide. In certain embodiments, the lines are about 50 nanometers to about 200 micrometers wide. In some embodiments 1-100 binding agents are bound to the surface of the substrate 102. In an embodiment, the array of lines spans the width of the substrate 102. In another embodiment, the array of lines spans the length of the substrate 102. In some embodiments, one or more binding agents 110 are bound to the substrate 102 in a pattern of spots and/or dots. In an embodiment, the spots/dots are about 25 nanometers to about 500 micrometers wide. In certain embodiments, the spots/dots are about 50 nanometers to about 200 micrometers wide. In an embodiment, an array of spots and/or dots covers a surface of the substrate.

In some embodiments, a binding agent 110 is bound to the entire surface of the substrate 102. For example, in an embodiment in which the substrate 102 is a slide, the entire surface of the slide can be coated with a binding agent 110 (e.g., red blood cells or an antibody).

The binding agents 110 are capable of binding to one or more substances in a blood sample (e.g., a whole blood, plasma, serum or RBC sample) or a saliva sample. In some embodiments, the binding agent 110 is an antibody to an antigen bound at the surface of a red blood cell or to human immunoglobulins or/and to a complement fraction (coated, e.g., adsorbed on the red blood cells) and the substance is the antigen. In some embodiments, the binding agent is native or hemolyzed phenotyped red blood cell or recombinant antigens and the substance is an antibody to the antigen bound at the surface of the red blood cells. In some embodiments, the binding agent is lectin or an universal anti-red blood cell antibody (e.g. anti-glycophorin A antibody) and the substance is red blood cells.

In some embodiments, the antibodies used as binding agents 110 or substances are those immunoglobulins that are specifically reactive with various antigenic determinants characteristic of particular blood groups. The antibodies may be IgA antibodies, IgM antibodies, IgG antibodies or mixtures thereof. In some embodiments, antibodies may be specifically reactive with red blood cell antigens characterizing the various major and minor blood group systems. Such blood group systems include, but are not limited to, the ABO system, the Rhesus (RH) system with in particular the antigens D (the absence of the D antigen being noted d), C, E, c, e and Cw, the Kell (KEL) system with in particular the four antigens K, k, $Kp^a$ and $Kp^b$, the Duffy (FY) system with in particular the antigens $Fy^a$ and $Fy^b$, the Kidd (JK) system with in particular the antigens $Jk^a$ and $Jk^b$, the MNS system with in particular the antigens M, N, S and s, as well as the antigen P1 from the P system, the Lutheran system with in particular the antigens $Lu^a$ and $Lu^b$, and the Lewis (LE) system with in particular the antigens $Le^a$ and $Le^b$.

The antibodies may be polyclonal and/or monoclonal or a mixture of monoclonals or functional fragments thereof, which include the domain of a F(ab')2 fragment, a Fab fragment, scFv, and VHH nanobodies. A functional antibody fragment can be (i) derived from a source (e.g., a transgenic mouse); or (ii) chimeric, wherein the variable domain is derived from a e.g. non-human origin and the constant domain is derived from a e.g. human origin or (iii) complementary determining region (CDR)-grafted, wherein the CDRs of the variable domain are from a e.g. non-human origin, while one or more frameworks of the variable domain are of e.g. human origin and the constant domain (if any) is of e.g. human origin. The antibodies can be isolated from natural source, i.e. living organism or cell culture or can be fully or partially synthetic antibodies. A synthetic antibody is an antibody having a sequence derived, in whole or in part, in silico from synthetic sequences that are based on the analysis of known antibody sequences. In silico design of an antibody sequence or fragment thereof can be achieved, for example, by analyzing a database of antibody or antibody fragment sequences and devising a polypeptide sequence utilizing the data obtained therefrom.

In some embodiments, the red blood cells used as binding agents 110 are native phenotyped red blood cells having known blood group surface antigens. In other embodiments, hemolyzed phenotyped red blood cells or "ghosts" may be used as binding agents 110 or substances. Ghosts are red blood cells that have been gently hemolyzed and have their hemoglobin removed, keeping all their antigenicity. In some embodiments, enzyme treated red blood cells may be used as binding agents 110. In some embodiments, blood group surface antigens isolated from membranes may be used as binding agents 110. In yet other embodiments, chemically synthesized polypeptide and polysaccharide blood group antigens as well as recombinant blood group antigens may be used as binding agents 110.

The binding agents 110 may be deposited onto the surface of the substrate 102 by techniques such as, but not limited to, hydrodynamic fluid confinement, ink jet printing, spray deposition, microspotting and/or microcontact printing. During or after deposition, the binding agents 110 may be immobilized onto the surface of the substrate 102 by, for example, electrostatic attractions, affinity interactions, hydrophobic/hydrophilic interactions, or covalent coupling.

In some embodiments, regions of the substrate 102 that do not have immobilized binding agents 110 and could provide non-specific binding sites may be treated with blocking agents such as, for example, non-fat milk protein, casein, and/or bovine serum albumin in a buffer.

In an embodiment illustrated in FIG. 2 that may be used for antigen typing or phenotyping, the binding agents 110 immobilized on the surface of the substrate 102 are an array of one or more antibodies each to a different antigen. In some embodiments, multiple antibodies to a single antigen are immobilized on the surface of the substrate 102. Each vertical line may represent a different antibody, e.g., anti-A, anti-B, anti-AB, anti-D, anti-C, anti-c, anti-Cw, anti-K, anti-k, anti-$Kp^a$, anti-$Kp^b$, anti-$Fy^a$, anti-$Fy^b$, anti-$Jk^a$, anti-$Jk^b$, anti-$Le^a$, anti-$Le^b$, anti-P1, anti-M, anti-N, anti-S, anti-s, anti-$Lu^a$ or anti-$Lu^b$.

In an embodiment illustrated in FIG. 3 that may be used for antibody screening and/or identification, the binding agents 110 immobilized on the surface of the substrate 102 are an array of one or more native or hemolyzed phenotyped red blood cells, membrane extracts or/and recombinant blood group antigens. Each vertical line represents a different red blood cell, for example, red blood cells RBCI, RBCII, RBCIII . . . RBCXX.

In an embodiment illustrated in FIG. 4 that may be used for antigen typing and antibody screening and/or identification (e.g., a "combo" test), more than one array of binding agents 110 (i.e., an array of antibodies to red blood cell antigens and an array of red blood cells) may also be immobilized onto the substrate 102. For example, a vertical line each of anti-A, anti-B, anti-AB, anti-D, anti-C, anti-c, anti-Cw, anti-K, anti-k, anti-$Kp^a$, anti-$Kp^b$, anti-$Fy^a$, anti-$Fy^b$, anti-$Jk^a$, anti-$Jk^b$, anti-$Le^a$, anti-$Le^b$, anti-P1, anti-M, anti-N, anti-S, anti-s, anti-$Lu^a$ or anti-$Lu^b$ antibodies may be bound to the surface of the substrate 102 and a vertical line each of red blood cells RBCI, RBCII, RBCIII . . . RBCXX may be bound to the surface of the substrate 102.

Referring again to FIG. 1, the dispenser 104 is configured to dispense a microfluidic or sub-microfluidic volume of one or more samples in a discreet path on the surface of the substrate 102. In some embodiments, the path spans the length of the substrate 102. In other embodiments, the path spans the width of the substrate 102. In certain embodiments, the width of the path is from about 25 nanometers to about 500 micrometers wide. In an embodiment, the dispenser 104 is also configured to dispense one or more binding agents 110 on the surface of the substrate 102.

In some embodiments, the dispenser 104 is moveable in the X-Y- and/or Z direction. Movement and functions of the dispenser 104 may be computer controlled.

In some embodiments, the dispenser 104 is a hydrodynamic flow confinement dispenser. In an embodiment, the hydrodynamic flow confinement dispenser is a microfluidic probe 200 (or vertical MFP) as described in U.S. patent application Ser. No. 13/881,989, which is incorporated herein. In an embodiment illustrated in FIGS. 5A and 5B, the microfluidic probe 200 may include a base layer 220, wherein processing liquid microchannels 223, 224 are provided together with immersion liquid microchannels 323, 324. Each channel is in fluid communication with an aperture 221, 222, 321, 322, each aperture located on a face of the base layer (not necessarily the same face), and preferably in close proximity. The channels 223, 224, 323, 324 also provide connection between motorized pumps and the apertures 221, 222, 321, 322. When moving the microfluidic probe 200 in the vicinity of a surface, processing liquid provided through the aperture 221 will combine with the immersion liquid and preferably inserts into immersion liquid provided via the apertures 321 and 322, as symbolized by the curved (thick) arrows if FIG. 5B. The latter are provided for the sake of understanding; their dimension are deliberately exaggerated. In this regard, the device is preferably configured such as to obtain a laminar flow. In some embodiments, the aperture dimensions may be a few tens of micrometers. The apertures are can be spaced apart by fifty micrometers or as much as hundreds of micrometers apart. As pairs of processing channels/apertures are used herein, the processing liquid can be re-aspirated at aperture 222 together with some of the immersion liquid. Note that the flow path between apertures 221 and 222 can be inverted, i.e. processing liquid can be injected from aperture 222 while aperture 221 can aspirate liquid. The processing liquid is essentially located nearby the apertures 221 and 222 and is surrounded by an immersion liquid that is essentially present in the vicinity of the head 200. A cover layer 210 closes the channels open on the upper face of the base layer, as depicted.

In addition, portions of the processing liquid microchannels are preferably provided as grooves 223', 224' in the layer thickness of the base layer 220, open on the upper face thereof. This way, forming a microchannel is easily achieved, in spite of its transverse dimensions (likely small, e.g., a few tens of micrometers). After assembly, the groove is closed by a portion of the cover layer 210. The groove may be engraved by a tool directly on the upper surface of the base layer 220. It can have any appropriate section shape, e.g. rounded, square, U or V section. The required tool is typically chosen according to the material of the base layer 220. In a variant, laser ablation can be contemplated. Most advantageously yet, deep reactive ion etching (DRIE) is used for fabrication of microchannels.

Figures 5A, 5B:
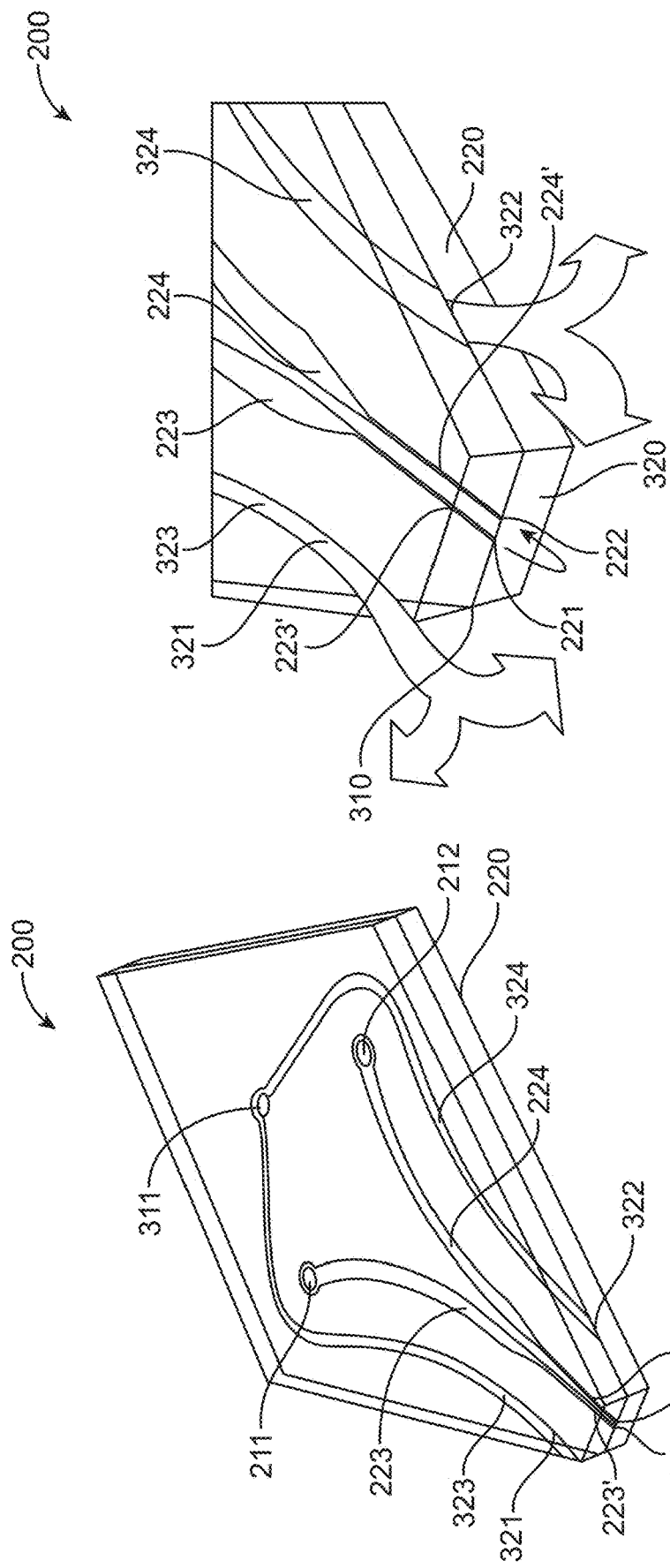
FIGS. 5A and 5B show a microfluidic probe of the prior art.

As depicted in FIG. 5B, the grooves 223', 224' extend up to respective apertures 221, 222. Similarly, immersion channels 223, 224 reach respective apertures 321, 324. In this example, channels and apertures are symmetrically arranged around the main axis of the upper face of the head. An aperture is directly formed at an end of the groove at the level of an edge 310 of the front face 320 of the base layer 220, which here again is easily machined. Said front end 320 is typically made acute, which allows for compact liquid deposition on a surface of interest, and leaves rooms for easy optical monitoring.

Referring to FIG. 5A, vias 211, 212 are provided on the cover layer 210. An additional via 311 is shown, which allows for relaying fluid communication to immersion channels 323, 324 (only one via is provided here, which feeds both immersion channels). Corresponding tubing ports connected to the vias can be provided (not shown). The channels have ends arranged such as to face the vias.

As depicted in FIGS. 5A and 5B, the microfluidic probe 200 includes two processing liquid microchannels. In some embodiments, the microfluidic probe 200 includes more than two processing liquid microchannels. In some embodiments, the microfluidic probe 200 may include 2-50 processing liquid microchannels (see FIG. 11). In some embodiments, the microfluidic probe 200 may include a heating element in at least one of the processing liquid microchannels. Heating the sample may increase the speed at which the antigens and antibodies react which may reduce test time.

Exemplary processing liquids include buffer, whole blood, RBCs, plasma, serum, or oil (e.g., mineral oil). Exemplary immersion liquids include mineral oil, buffer, water, and/or saline.

Figure 6:
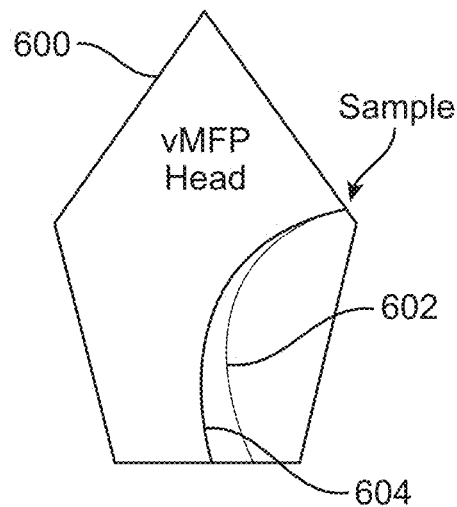
FIG. 6 shows a top view of a microfluidic probe according to an embodiment of the invention.

In some embodiments, the microfluidic probe includes structures for separation of plasma from red blood cells in a whole blood sample. In some embodiments, the separation may be achieved by size and/or by capillary forces. FIG. 6 illustrates an embodiment of a microfluidic probe 600 having at least two processing liquid microchannels of differing dimensions. The probe is configured such that it may be used with whole blood samples or with RBC-containing samples (i.e., RBCs in plasma) without clogging. A first microchannel 602 is sized to exclude red blood cells in a whole blood sample. A second microchannel 604 is sized to allow red blood cells from a sample to flow therethrough. In an embodiment in which the processing liquid microchannels have a circular cross section, the first microchannel 602 has a diameter less than 6 micrometers. In some embodiments, the diameter of the first microchannel is less than 4 micrometers or less than 2 micrometers or less than 1-2 micrometers. In some embodiments, the second microchannel 604 has a diameter greater than about 7 micrometers. The diameter of red blood cells is about 6-8 micrometers. Having the larger diameter, the second microchannel 604 will allow red blood cells to flow therethrough. The cross section of the microchannel may be any appropriate shape including circular, oval, and elliptical. In some embodiments, inner surfaces of the processing liquid microchannels 602 and 604 may be coated with a material e.g., heparin, that prevents blood components from binding to the inner surfaces. The whole blood sample may also be anti-coagulated with, for example, heparin, citrate or EDTA to prevent the blood from clotting.

Figure 7:
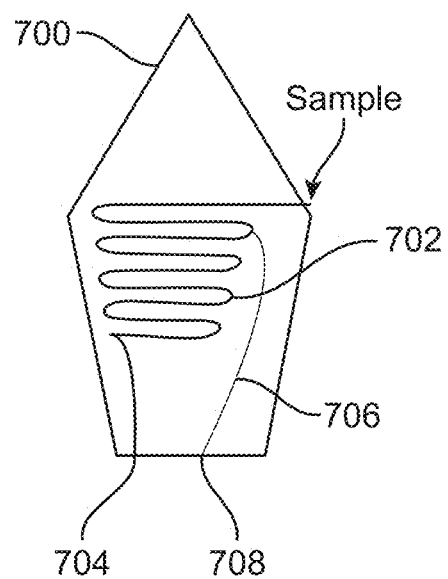
FIG. 7 shows a top view of a microfluidic probe according to another embodiment of the invention.

FIG. 7 illustrates an embodiment of a microfluidic probe 700 having a tortuous microchannel 702 in fluid communication with a first aperture 704. The diameter of the tortuous microchannel 702 is sized to retain RBCs from a whole blood sample. A smaller diameter capillary 706 branches off the tortuous microchannel 702 and is in fluid communication with a second aperture 708. The capillary 706 allows red blood cell-free plasma to flow therethrough.

Microfluidic probes may be formed of material that is compatible with the fluids flowing through the channels. Exemplary compatible materials include, but are not limited to, silicon, silica, polydimethylsiloxane (PDMS), gallium arsenide, glass, ceramics, quartz, polymers such as neoprene, Teflon™, polyethylene elastomers, polybutadiene/SBR, nitrites, nylon, and/or metals. The inner surface of the channels may also be coated with suitable material to reduce the affinity between the fluid components and the channels themselves.

Referring again to FIG. 1, the light source 106 is configured to irradiate the surface of the substrate 102. Depending on the signal to be detected, the light source 106 may provide light ranging from the visible range to the near infrared range. Exemplary light sources include lasers and light emitting diodes.

The detector 108 is configured to detect light emitted from the surface of the substrate 102. In some embodiments, detection is achieved by colorimetric, fluorescent or luminescent detection. In some embodiments, detection is achieved by imaging such as by photography or by electronic detectors. Exemplary electronic detectors include photodiodes, charge-coupled device (CCD) detectors, or complementary metal-oxide semiconductor (CMOS) detectors.

The analog signal from the detector 108 is digitized by an analog-to-digital converter 110. The digitized signal is processed by a microprocessor 112 to obtain at least one value or intensity of detected light that is store in memory 114 and/or displayed on an optional display 116.

By using appropriate electronics and software, the system 100 can be programmed to know the identity and location of specific substances bound to the binding agents 110 on the surface of the substrate 102. The identity and location of the substances can be correlated with signals generated so that a particular blood grouping can be determined and identified to the tester. Additionally, statistical software may be included so as to combine and formulate the results from the various repetitions and/or dilutions of the binding agents 110 provided on the substrate 102. In this manner, the signals obtained from a multiplicity of substances may be factored together and a statistically significant result displayed to the tester.

Methods

The system 100 may be used to perform antigen typing, antibody screening/identification, combined antigen typing and crossmatching. Additionally the system 100 is used for detection of grouping and phenotyping, screening and/or identification of antibodies, cross-matching and direct antiglobulin test.

Figure 8:
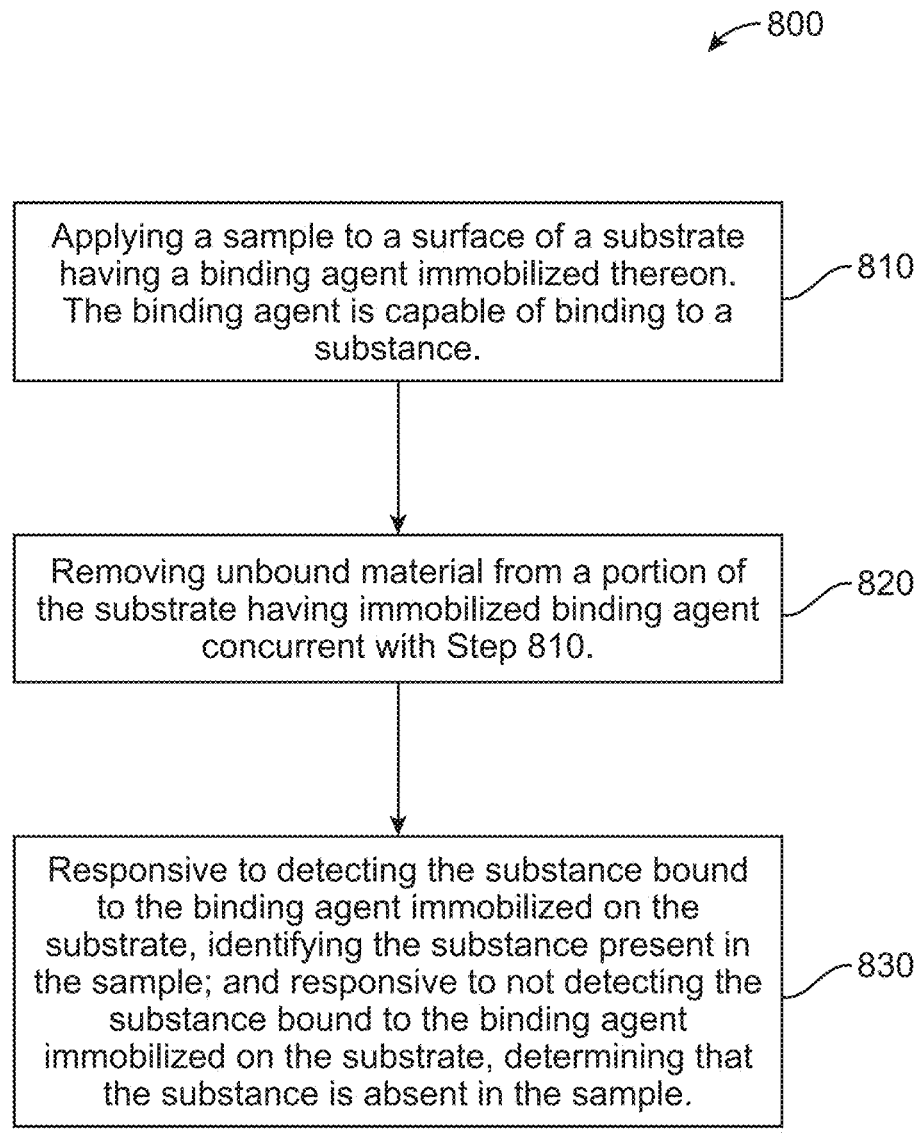
FIG. 8 is a flow chart showing a method of applying a sample to a surface of a substrate having previously immobilized native or hemolyzed phenotyped RBCs and/or antibodies to RBCs using the system of FIG. 1 according to an embodiment of the invention.

Referring to FIG. 8, a method 800 for antigen typing and/or antibody screening and/or identification will now be described. The method 800, for example, may be executed with the aforementioned system illustrated in FIG. 1.

In exemplary step 810, a sample is applied to a wet or dry substrate 102 having one or more binding agents 110 immobilized thereon, wherein the one or more binding agents 110 are capable of binding to one or more substances in the sample. In an antigen typing embodiment shown in FIG. 2, the sample and substance is patient or donor RBCs treated or not treated by enzyme and the binding agents 110 immobilized on the surface of the substrate 102 are antibodies to red blood cell (RBC) antigens. The RBC sample may be provided by separating whole blood into RBCs and plasma by, for example, centrifugation. The resulting RBCs can be used "as is" or may be diluted. In some embodiments, the RBCs are diluted to about 0.1 to 50%. In some embodiments, the RBCs are diluted to between about 0.5-20%. In certain embodiments, the RBCs are diluted to between about 0.6 to 5%. In some embodiments, the RBCs are diluted to greater than 50%.

In an antibody screening and/or identification embodiment shown in FIG. 3, the sample is patient or donor plasma, the binding agents 110 immobilized on the surface of the substrate 102 are native or hemolyzed phenotyped RBCs, chemically synthesized polypeptide, natural or synthesized polysaccharide blood group antigens, or recombinant blood group antigens and the one or more substances are antibodies to RBC antigens, the recombinant red blood cell antigens or red blood cell membrane extracts.

In an embodiment shown in FIG. 4, the antigen typing embodiment shown in FIG. 2 is combined with the antibody screening and/or identification embodiment shown in FIG. 3. In this embodiment (e.g., a "combo" assay), a first portion of the substrate has immobilized phenotyped RBC which may be native or hemolyzed and a second portion has immobilized antibodies to RBC antigens.

Figure 10:
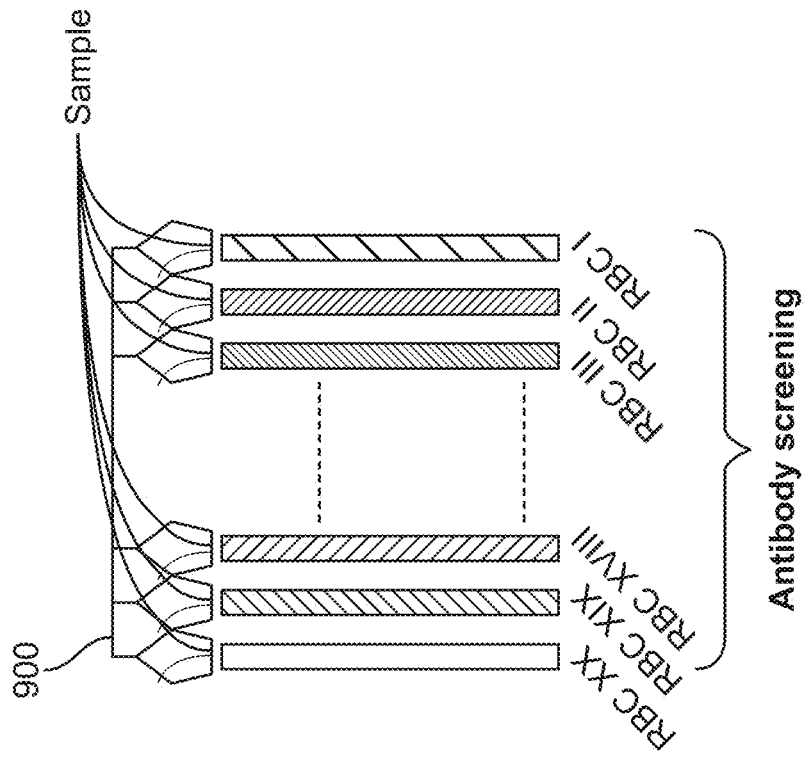
FIGS. 9 and 10 show multiple microfluidic probes in parallel connected to a single sample or different samples according to an embodiment of the invention.
Figure 9:
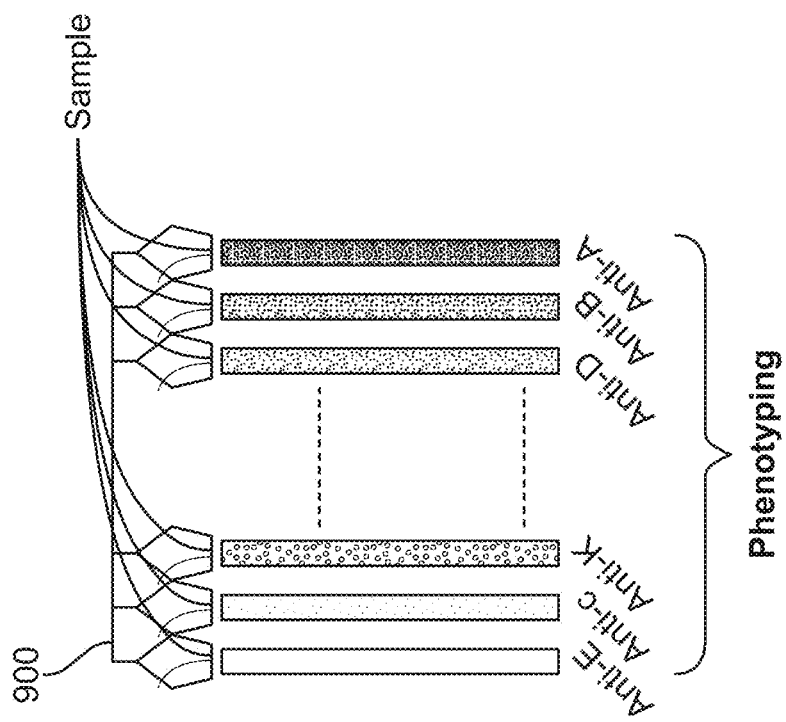

In an embodiment, one or more samples are applied with one or more microfluidic probes. In another embodiment, one microfluidic probe is used for each sample (FIGS. 2-3). Each sample is applied to the substrate 102 coated with binding agents 110 in a direction perpendicular to the line of binding agents 110 such that the sample is applied to each of the binding agents 110 coated on the substrate 102. In yet another embodiment, an array of probes in parallel, probe array 900, are connected to the same or different samples (FIGS. 9-10). The probe array 900 applies the same or different samples to all the binding agents 110 at once. For a new sample, the channels in the probe array 900 are, for example, rinsed to remove the first sample, the probe array 900 are moved together to another set of binding agents 110 and the new sample is applied to the new set of binding agents 110. For each new sample, the process of rinsing and moving the probe array 900 is repeated. In some embodiments, a plurality of probe arrays 900 are used to test multiple samples each against multiple binding agent 110 at one time.

Figure 11:
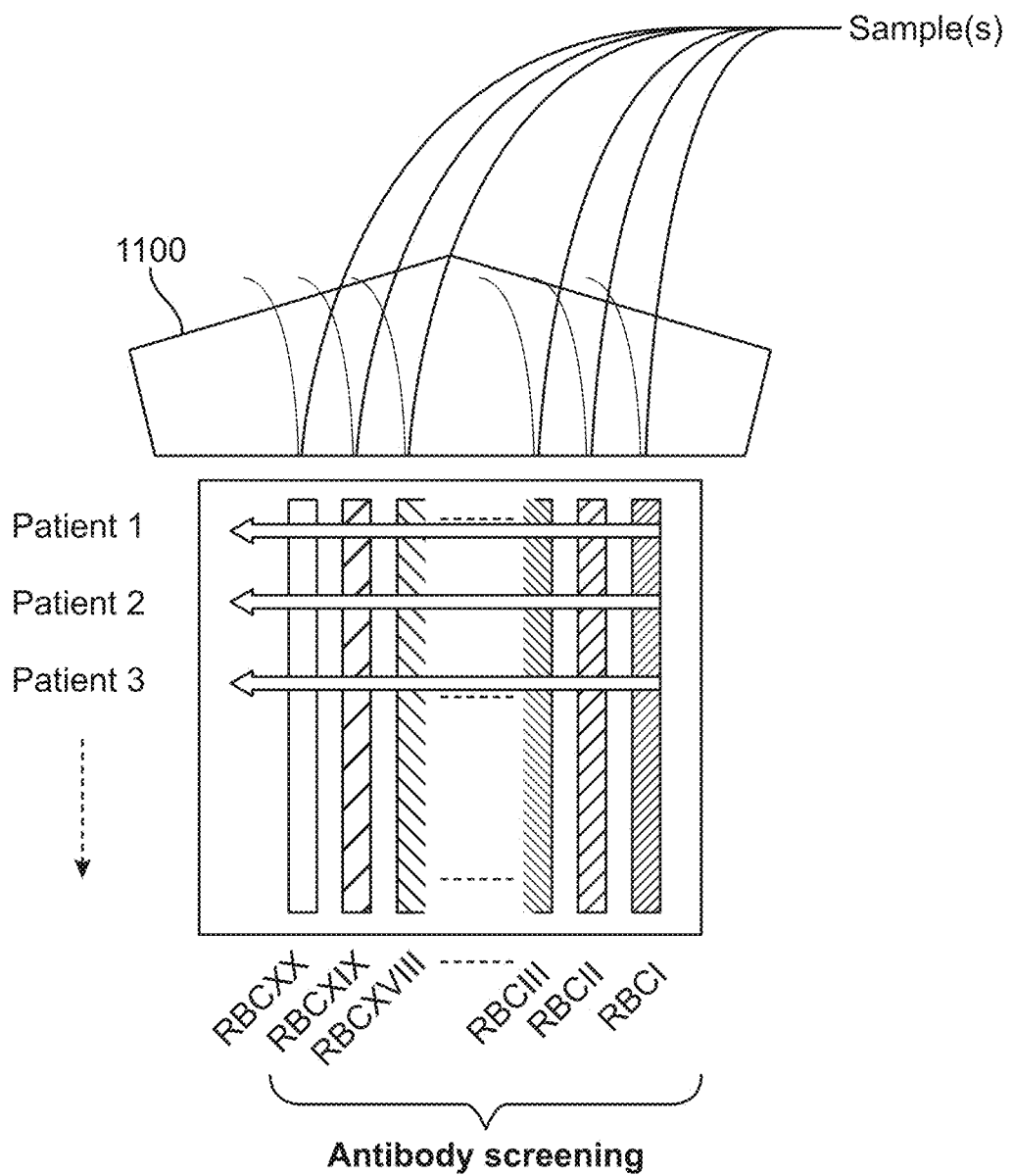
FIG. 11 shows a microfluidic probe having a plurality of processing liquid microchannels, which may be connected to a single sample or multiple samples, according to an embodiment of the invention.

In an embodiment shown in FIG. 11, a microfluidic probe 1100 includes a plurality of processing liquid microchannels. The plurality of processing liquid microchannels may be used to deposit one or more samples (i.e., the same or different samples) and/or binding agents 110 onto the surface of the substrate 102. In some embodiments, the microfluidic probe includes 2-100 processing liquid microchannels. In other embodiments, each of the probes in the probe arrays 900 (shown in FIGS. 9-10) includes a plurality of microchannels. In a "combo" assay embodiment, the microfluidic probe 600 shown in FIG. 6 is used to deposit one or more samples onto the embodiment shown in FIG. 4 in which a first portion of the substrate has immobilized phenotyped RBC, which may be native or hemolyzed, and a second portion has immobilized antibodies to RBC antigens.

In exemplary step 820, unbound material, e.g., red blood cells and/or antibodies, is removed from at least a portion of the substrate 102 having immobilized binding agent thereon. The unbound material may be removed by washing the surface of the substrate 102 with, for example, buffer, water or saline. In an embodiment, a microfluidic probe may be used to remove unbound material concurrent with step 810 by pumping a wash solution (e.g., an immersion liquid) through one or more processing liquid microchannels.

In exemplary step 830, substances bound to the one or more binding agents 110 immobilized on the substrate 102 are detected and the substances present in the sample are identified. The absence of substances bound to the binding agents may also be determined. In the antigen typing embodiment, the red color of RBCs bound to the RBC antibodies may be detected visually or spectrophotometrically. The RBCs bound to the RBC antibodies may also be detected by secondary labeling detection including, for example, colorimetric, fluorescent or chemiluminescent conjugated antibodies. In an antibody screening and/or identification embodiment, the antibodies bound to the RBC antigens may be detected by specific secondary labeling detection.

Figure 12:
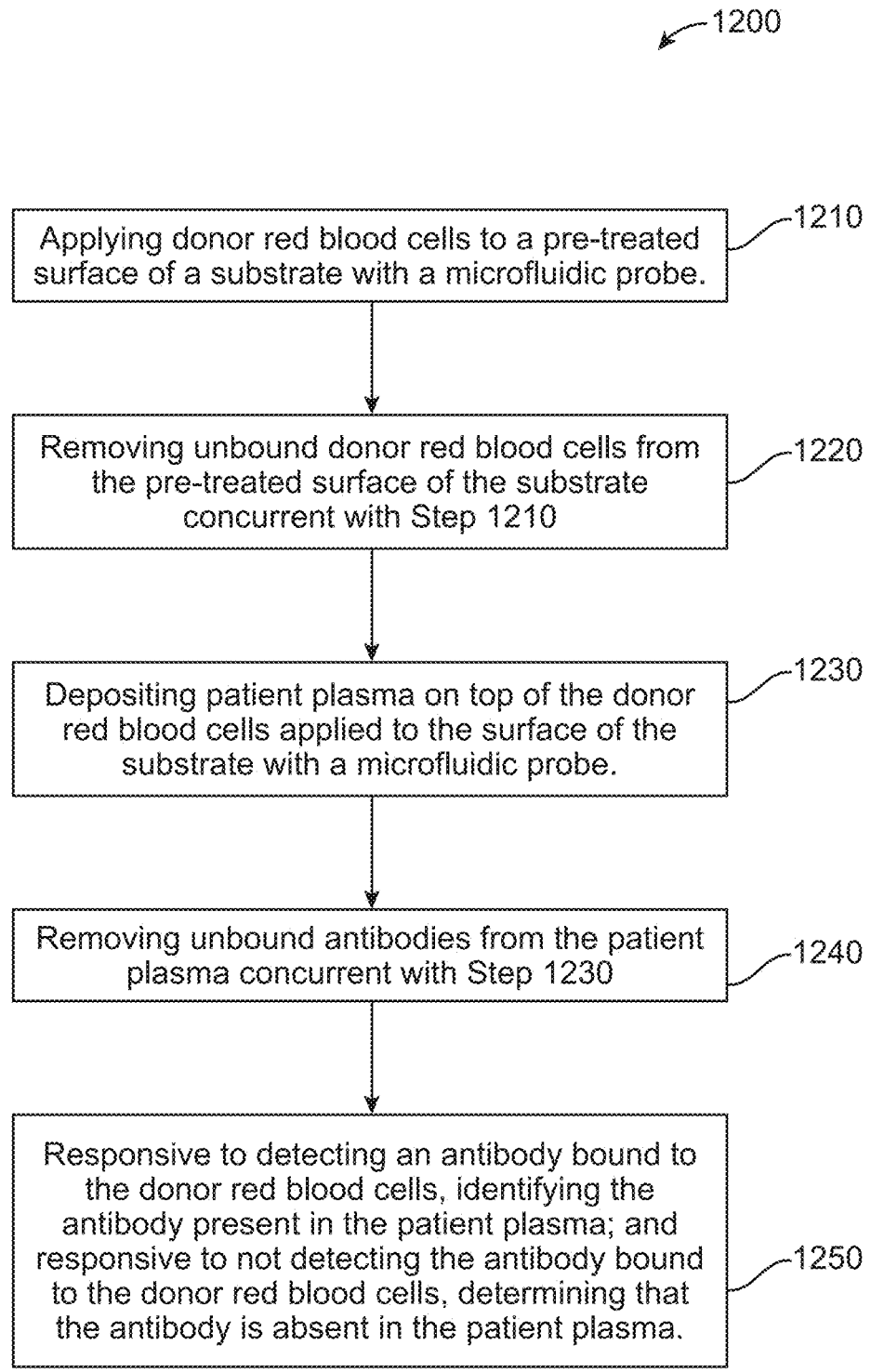
FIG. 12 is a flow chart showing a method of crossmatching patient plasma with a potential donor's red blood cells according to an embodiment of the invention.

Referring to FIG. 12, a method 1200 for cross-matching will now be described in which a microfluidic probe is used to deposit donor red blood cells and patient plasma. This method tests the compatibility of a donor's RBCs with a patient's plasma. The method 1200, for example, may be executed with the aforementioned system illustrated in FIG. 1.

In exemplary step 1210, a donor's red blood cells are applied to a wet pre-treated surface of a substrate with the microfluidic probe. The donor's red blood cells may be native or hemolyzed. In some embodiments, the donor's red blood cells are also phenotyped. In some embodiments, these RBCs are applied to the surface of the substrate in an immersion liquid to maintain the antigenicity of the red blood cells. In some embodiments, the surface of the substrate is pre-treated with binding agents such as, for example, lectins, chemical agents or universal anti-RBC antibodies such as, for example, anti-glycophorin A antibody.

In exemplary step 1220, unbound donor red blood cells are removed by washing the surface of the substrate 102 with, for example, buffer, water or saline. In an embodiment, a microfluidic probe may be used to remove unbound donor red blood cells concurrently with step 1210 by pumping a wash (immersion) solution through one or more processing liquid microchannels.

In exemplary step 1230, a patient plasma sample is deposited on top of the donor RBCs applied to the surface of the pre-treated substrate in step 1210. In an embodiment, the same probe as used in step 1210 is used to deposit the patient plasma. Either the same microchannel or a different microchannel as in step 1210 may be used to deposit the patient plasma. If the same microchannel is used as in step 1210, the microchannel can be flushed with, for example, buffer between uses or a "slug" of buffer, oil or air may be used to separate the donor RBCs from the patient sample. In another embodiment, a different microfluidic probe is used between this step and step 1210 to prevent cross contamination.

In exemplary step 1240, unbound antibodies from the patient plasma sample are removed by washing the surface of the substrate 102 with, for example, buffer, water or saline. In an embodiment, a microfluidic probe may be used to remove unbound antibodies with step 1230 by pumping a wash solution through one or more processing liquid microchannels.

In exemplary step 1250, responsive to detecting an antibody bound to the donor red blood cells, antibody present in the patient plasma is detected (e.g., by a secondary labeled antibody) and responsive to not detecting the antibody bound to the donor red blood cells, antibody absent in the patient plasma is determined.

In another cross-matching method (e.g., a minor cross-matching method), a microfluidic probe is used to deposit patient RBCs and donor plasma. This method tests the compatibility of a patient's plasma with a donor's RBCs and is important in the situation where whole blood is transfused into a patient rather than just RBCs or where a medically relevant amount of donor plasma remained in the separated RBCs transfused to the patient. The minor cross-matching method may, for example, be executed with the aforementioned system illustrated in FIG. 1.

One advantage of the microfluidic probe is its ability to deposit in physiological immersion liquid which allows for maintaining the antigenicity of the red blood cells. This provides for additional possible uses for the probe. In some embodiments, a system for blood typing includes a substrate having one or more binding agents immobilized in discreet locations, wherein the one or more binding agents are capable of binding to native or hemolyzed red blood cells; a dispenser configured to dispense these native or hemolyzed phenotyped red blood cells onto the substrate and to remove unbound red blood cells from the substrate; a dispenser configured to deposit a patient plasma sample on top of the red blood cells applied to the surface and to remove unbound antibodies and a detector is configured to detect antibodies. The previously described cross-matching is one example.

Antibody screening is another example. Phenotyped RBCs are deposited by the probe on a pre-treated surface as in the cross-matching assay. A wash is applied and then plasma containing antibodies are deposited and identified.

EXAMPLES

Example 1: Antigen Typing

The objective of this analysis is to identify, by means of specific monoclonal or polyclonal antibodies, the blood group antigens present at the surface of red blood cells from donors or from patients (group ABO, RH, Kell, Duffy, Kidd, Lewis, etc.).

In order to demonstrate the possibility of grouping/phenotyping red blood cells with the technology of the invention, the surface of the substrate 102 is used to immobilize the anti-red blood cell antibodies and a microfluidic probe 200 used to dispense patient red blood cells or whole blood sample and to remove unbound red blood cells. The red color of the RBCs bound to anti-erythrocytes antibodies is then visually detected.

1.1—Material

In this example, the binding agents 110 are anti-erythrocyte antibodies. The surface of the substrate 102 is a polystyrene 96-wells flat bottom plates. Antibodies are deposited with an ink-jet or contact printer as spots on the wells bottoms. Each well contains at least one spot of each antibody specificity. In this example, antibodies are diluted in PBS buffer (pH 7.4) at concentration ranging from 10 to 500 µg/mL and bound to the surface of the substrate 102 by passive absorption. After depositing the antibodies on the surface, the substrate is saturated by contact with PBS supplemented with 1% BSA to prevent non-specific binding of sample components and subsequently air dried.

In this example, used antibodies are:
Anti-A IgM clone 15750F7 (Bio-Rad),
Anti-D IgG clone BRAD3 (IBGRL),
Anti-K1 IgG clone MID11G4 (Bio-Rad).

1.2—Test Description

In order to demonstrate the feasibility and verify the specificity of the grouping according to the technology, each spot is individually tested. An adequate buffer (processing liquid) is dispensed into the wells in order to cover the whole well surface. The microfluidic probe is then positioned above an antibody spot. In a first step, a suspension of RBCs or whole blood is flown over the spot to bring RBCs and antibodies into contact. In a second step, the flow is switched to a washing buffer in order to remove unbound RBCs. At the end, the presence or absence of red blood cells attached to the spotted antibody is detected visually or spectrophotometrically.

Example 2: Antibody Screening/Identification

In order to demonstrate the possibility of antibody screening and identification with the technology of the invention, the surface of the substrate 102 is used to immobilize native or hemolyzed phenotyped red blood cells via poly-L-lysine (PLL). For this application, the microfluidic probe 200 is designed to perform heating and sequential chemistry. The probe is used to deposit patient plasma serum or whole blood sample, to remove unspecific antibodies and to dispense labeled anti-Fc antibody conjugate to detect bound antibodies.

2.1—Material and Reagents 2.1.1. Sensitization of the Surface of the Substrate 102 with PLL In this example, the surface of the substrate 102 is a polystyrene 96-wells flat bottom plates. A 25 µg/ml of PLL of molecular weight 70 000-130 000 in PBS, pH 7.4 is dispensed into each well and incubated for 18 hours at ambient temperature. At the end of this step, the wells are washed in PBS pH 7.4 supplemented with 0.05% Tween-20, and then used to immobilize the cells.

2.1.2. Immobilization of Cells on the Surface

In this example, the binding agents 110 are native or hemolyzed phenotyped red blood cells. Cells are deposited with an ink-jet or contact printer as spots on the PLL-coated well bottoms. Each well contains at least one spot of each phenotype. In this example, 20 to 50% cell suspensions in buffer supplemented with a preservative component. After deposition, the substrate is washed to remove unbound cells and then saturated by contact with PBS supplemented with 1% BSA and 1 M dextrose to prevent non-specific binding of sample components and cells preservation. After an overnight incubation, the saturation buffer is removed and the surface is air dried.

In this example, used binding agents are three native or hemolyzed phenotyped red blood cells typically used for antibody screening.

2.2. Test Description

Each spot of cells is individually tested. An adequate buffer (processing liquid) is dispensed into the wells in order to cover the whole well surface. The microfluidic probe is then positioned above a spot. In a first step, the patient plasma serum or whole blood is flown over the spot to bring the sample and RBCs into contact. The probe is set up to heat the reaction area at 37° C. In a second step, the sequential process is applied: washing in order to remove unspecific antibodies, dispensing of labeled anti-Fc antibody conjugate and a final washing to remove unbound labeled anti-globulin antibody. At the end, the presence or absence of antibody attached to native or hemolyzed phenotyped red blood cells is detected by colorimetric, fluorescent or luminescent.

Example 3: Cross-Matching

In order to demonstrate the possibility of performing cross-matching with the technology of the invention, the microfluidic probe 200 is used to perform all steps from immobilization of donor red blood cells via poly-L-lysine (PLL) to final reaction detection. This microfluidic probe 200 is designed to perform heating and sequential chemistry. The probe is also used to deposit patient plasma serum or whole blood sample and to remove unspecific antibodies. A labeled anti-Fc antibody conjugate is used to detect the bound antibodies.

3.1—Material and Reagents

3.1.1. Sensitization of the Surface of the Substrate 102 with PLL

In this example, the surface of the substrate 102 is a polystyrene 96-wells flat bottom plates. A 25 µg/ml of PLL of molecular weight 70 000-130 000 in PBS, pH 7.4 is dispensed into each well and incubated for 18 hours at ambient temperature. At the end of this step, the wells are washed in PBS pH 7.4 supplemented with 0.05% Tween-20, and then used to immobilize the cells.

3.1.2. Test Description

An adequate buffer (processing liquid) is dispensed into the PLL-coated wells in order to cover the whole well surface. The microfluidic probe 200 is then positioned above the surface and the sequential process is applied: deposition of prewashed donor red blood cells, washing step to remove unbound cells, flowing of the patient plasma serum or whole blood at 37° C., washing to remove unspecific antibodies, dispensing of labeled anti-Fc antibody conjugate and a final washing to remove unbound labeled anti-globulin antibody.

At the end, the presence or absence of antibody attached to donor red blood cells is detected by colorimetric, fluorescent or luminescent.

Example 4: Direct Antiglobulin Test

The objective of this analysis is to identify, by means of specific monoclonal or polyclonal antibodies, IgGs and/or C3d complement fraction coated on in vivo sensitized RBCs.

In order to demonstrate the possibility to detect sensitized RBCs with the technology of the invention, the surface of the substrate 102 is used to immobilize the anti-IgGs and anti-C3d antibodies. A microfluidic probe 200 is used to dispense prewashed patient red blood cells and to remove unbound red blood cells. The red color of the RBCs bound to specific antibodies is then visually detected.

4.1—Material

In this example, the binding agents 110 are anti-IgGs and anti-C3d antibodies. The surface of the substrate 102 is a polystyrene 96-wells flat bottom plates. Antibodies are deposited with an ink-jet or contact printer as spots on the well bottoms. Each well contains at least one spot of each antibody specificity. In this example, antibodies are diluted in PBS buffer (pH 7.4) at concentration ranging from 10 to 500 µg/mL and bound to the surface of the substrate 102 by passive absorption. After depositing the antibodies on the surface, the substrate is saturated by contact with PBS supplemented with 1% BSA to prevent non-specific binding of sample components and subsequently air dried.

In this example, used antibodies are:
Polyclonal rabbit anti-human-IgG (Bio-Rad),
Anti-C3d IgG clone 053A714 (Bio-Rad).

4.2—Test Description

In order to demonstrate the feasibility and verify the specificity of the test, the reactions are carried out in a unitary manner. In this case, each spot is individually tested. An adequate buffer (processing liquid) is dispensed into the wells in order to cover the whole well surface. The microfluidic probe is then positioned above an antibody spot. In a first step, a suspension of RBCs is flown over the spot to bring RBCs and antibodies into contact. In a second step, the flow is switched to a washing buffer in order to remove unbound RBCs. At the end, the presence or absence of red blood cells attached to the spotted antibody is detected visually or spectrophotometrically.

Example 5: Antigen Typing—Singleplex and Multiplex Grouping/Phenotyping

The objective of this analysis was to identify, by using specific monoclonal or polyclonal antibodies, the blood group antigens present at the surface of red blood cells from donors or from patients (group ABO, RH, Kell, Duffy, Kidd, Lewis, etc.).

To demonstrate the possibility of phenotyping/grouping red blood cells with the technology of the invention, an anti-red blood cell antibody was immobilized on the surface of the substrate and a microfluidic probe was used to dispense patient red blood cells concurrent with removing unbound red blood cells. The red color of the red blood cells bound to anti-erythrocytes antibodies was then visually detected, and was used to determine the antigenic specificities.

A. Singleplex Grouping of A-Positive Red Blood Cells

Materials

In this example, the binding agent was anti-red blood cell antibody, and more particularly a murine IgM anti-A mAb (Bio-Rad clone 15750F7). For this experiment and all the subsequent experiments, the substrate was a polystyrene slide (TED PELLA, INC.; product #260225). Antibody was deposited with an ink-jet printer as rows of spots on the slide. Each spot was clearly identified by X,Y coordinates. The spot size was about 250 μm in diameter. The spots were aligned with each other and were spaced apart by about 50-60 μm. The purified anti-A IgM antibody was diluted in PBS buffer (pH 7.4) at a concentration ranging from 10 to 500 μg/mL and was bound to the surface of the substrate 102 by passive absorption. After depositing the antibody on the surface, the substrate was treated with 1% BSA in PBS to prevent non-specific binding of sample components. The slides thus prepared were air dried and were stored at 4° C. until use. The microfluidic probe used in this and subsequent examples was a probe with 4 channels, each having dimensions of 100 μm×100 μm. To obtain an adequate hydrodynamic flow confinement, channel 2 was used to dispense sample and channels 1 and 3 were used to aspirate sample. Red blood cell suspensions having different phenotypes (A positive and O positive red blood cells) were used as samples.

Method

To demonstrate the feasibility and verify the specificity as well as the reproducibility of the grouping according to the technology, each spot was tested one after another with the same red blood cell solution (e.g., two A-positive red blood cells as well as two A-negative red blood cells (O red blood cells)). In this example, the red blood cells were washed in 0.9% isotonic saline solution and suspended at 50% in physiologic water. With the channel 2 of the microfluidic probe, 2 μl of the diluted red blood cell suspension was aspirated at 1.6 μl/min. To wet the slide, sufficient buffer (processing liquid) was dispensed onto the slide to cover the whole surface. The microfluidic probe was then positioned above the slide and hydrodynamic flow confinement was then set up. When the hydrodynamic flow confinement was stabilized, the movement of the microfluidic probe was programmed to move at a rate of 0.02 mm/s and to follow a straight line passing through the aligned spots. During movement of the probe, the red blood cells dispensed were either in contact with the saturated surface of the substrate 102 or were in contact with the spotted antibody. Red blood cells having the correct antigenic specificity bound immediately to the immobilized antibodies. Due to the continuous deposition and aspiration of cells and buffer processing fluid, the unbound red blood cells were removed concurrently with the binding of red blood cells. After deposition/aspiration of the red blood cells, the presence or absence of red blood cells attached to the spotted antibody was detected by camera image capture. Knowing the position of each spot on the substrate, it was possible to confirm if the antigens were present at the surface of red blood cells being tested, and thus to identify the blood group specificity of the red blood cells being tested.

Figures 13A, 13B:
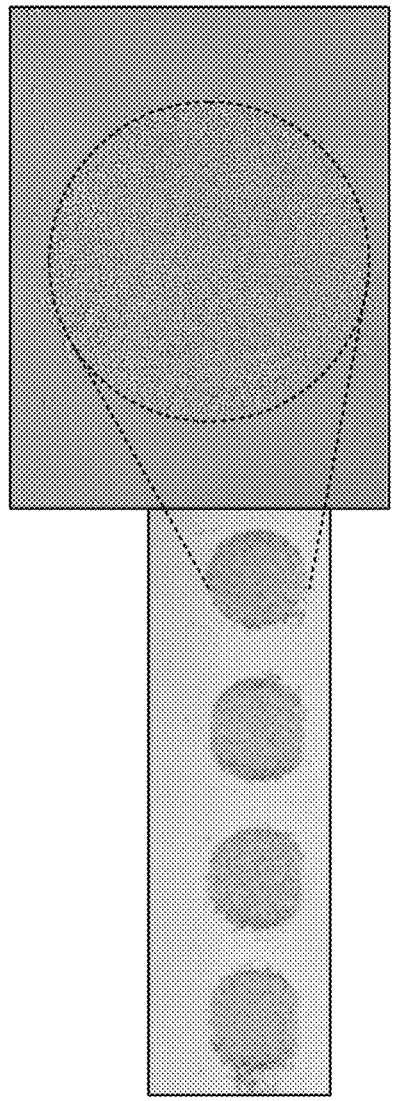
FIGS. 13A and 13B show results from singleplex antigen typing using a microfluidic probe as described in Example 5A.

To determine if antigens were present at the surface of A-positive and A-negative RBCs, two A-positive red blood cells and two A-negative red blood cells were tested by depositing the RBCs on 20 spots. The test results for four of the 20 spots having A-positive red blood cells bound are shown in FIG. 13A. A close up view of the fourth spot is shown in FIG. 13B. The A-positive red blood cells bound strongly to the entire spot surface, whereas the A-negative red blood cells did not bind at all (not shown). These results demonstrate that the binding observed is specific: the red blood cell binding occurs only when an antigen-antibody pair is involved. The results also demonstrate that the A-positive red blood cells can be clearly distinguished from the A-negative red blood cells such that the A antigen at the surface of red blood cells can be identified. Additionally, these results show that the microfluidic probe can be used in a singleplex antigen typing method in which a microfluidic probe is used to apply RBCs to anti-red blood cells antibodies on a solid substrate while concurrently removing unbound RBCs.

The applicant also found that when red blood cells with a lower antigen density were evaluated, the spot surface covered by the red blood cells was less dense.

B. Multiplex Grouping of A and D Positive Red Blood Cells

In this example, the same aliquot of red blood cells (and therefore less sample) was used to react separately with an immobilized murine IgM anti-A monoclonal antibody (mAb) as well as immobilized human IgG anti-D mAb.

Materials

The binding agents were anti-red blood cell antibodies: murine IgM anti-A (clone 157 50 F7) and human IgG anti-D mAbs (clone Brad3). Antibodies were deposited manually as spots on the polystyrene slide. Each spot was clearly identified by the X,Y coordinates. In this case, the spot size was about 1.5 mm in diameter. The spots with the same antibody specificity were aligned with each other and were spaced apart from each other by about 200 μm. The antibodies used had been purified and diluted in PBS buffer (pH 7.4) at a concentration ranging from 10 to 500 μg/mL. The diluted antibodies were bound to the surface of the substrate by passive absorption. After depositing the antibodies on the surface, the substrate was saturated with PBS supplemented with 1% BSA to prevent non-specific binding of sample components. The slides were air dried and stored at 4° C. until use. The conditions used to obtain an adequate confinement were as follows: channel 1: aspirate, channel 2: dispense, and channel 3: aspirate. Red blood cell suspensions having different A and D phenotypes (A+, A−, O+ and O−) were used as samples.

Method

To demonstrate the feasibility and verify the specificity of grouping/phenotyping using the microfluidic probe technology, each spot was tested one after another with the same red blood cell solution. In this example, the red blood cells were first washed in 0.9% isotonic saline solution and were suspended at 50% in physiologic water. 1.5 μl of red blood cell suspension was aspirated at 1.5 μl/min. To wet the slide, sufficient PBS buffer (processing liquid) was dispensed onto the slide to cover the whole surface. The microfluidic probe was positioned above the slide and hydrodynamic flow confinement was then set up. When hydrodynamic flow confinement was stabilized, the movement of the microfluidic probe following the X-axis or Y-axis was programmed at 0.02 mm/s so that a straight line passing through the aligned spots was drawn. During movement of the probe, the red blood cells dispensed were either in contact with the saturated surface of the substrate or were in contact with one of the spotted antibodies. Red blood cells having the correct antigenic specificity bound immediately to the immobilized antibodies. Due to the continuous deposition and aspiration of cells and buffer processing fluid, the unbound red blood cells were removed concurrent with binding of red blood cells. After deposition/aspiration of the red blood cells, the presence or absence of red blood cells attached to the spotted antibody was detected by camera image capture. Knowing the position of each specific antibody on the substrate, it was possible to identify which antigens were present at the surface of red blood cells being tested, and thus to identify the blood group specificity of the red blood cells being tested.

Figure 14A:
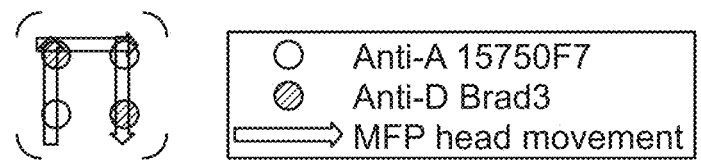
FIGS. 14A-14D show results from multiplex antigen typing using a microfluidic probe as described in Example 5B. A-positive red blood cells bound strongly to the scanned region of the spot surface at which the anti-A mAb was immobilized (FIG. 14A), whereas the A-negative red blood cells did not bind at all (FIG. 14B). The D-positive red blood cells also bound strongly to the scanned region of the spot surface at which the anti-D mAb was immobilized (FIG. 14C), whereas the D-negative red blood cells did not bind at all (FIG. 14D).
Figure 14A:
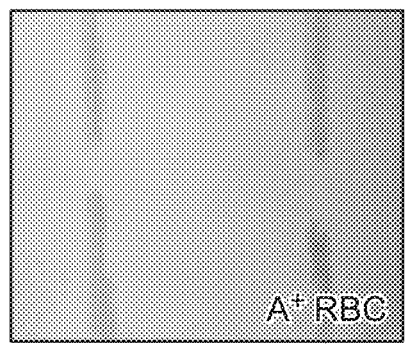
Figure 14B:
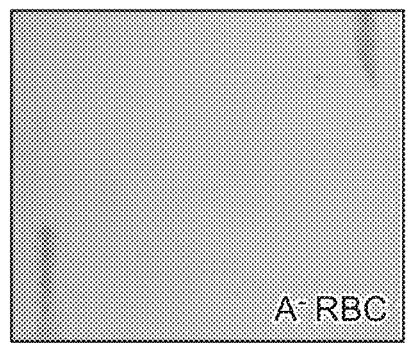
Figure 14C:
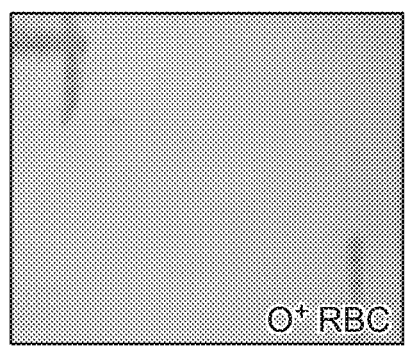
Figure 14D:
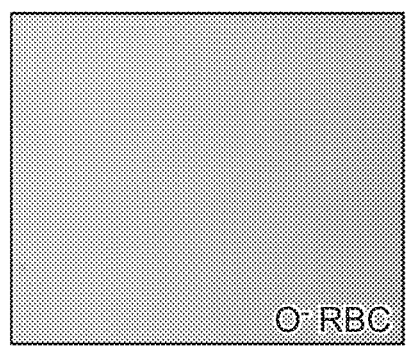

A-positive red blood cells (A+, A−) and D-positive red blood cells (A+, O+), as well as A-negative (O− and O+) and D-negative red blood cells (O− and A−) were used as samples and were deposited in a line on 2 spots each. The A-positive red blood cells bound strongly to the scanned region of the spot surface at which the anti-A mAb was immobilized (FIG. 14A), whereas the A-negative red blood cells did not bind at all (FIG. 14B). The D-positive red blood cells also bound strongly to the scanned region of the spot surface at which the anti-D mAb was immobilized (FIG. 14C), whereas the D-negative red blood cells did not bind at all (FIG. 14D). These results demonstrate that the binding observed was specific: the spot/red blood cell binding occurs only when an antigen-antibody pair is involved. These results also demonstrate the feasibility of two-parameter multiplexed grouping/phenotyping of red blood cells using the microfluidic probe technology of the invention. Additionally, these results show that the microfluidic probe can be used in a multiplex antigen typing method in which a microfluidic probe is used to apply RBCs to anti-red blood cells antibodies on a solid substrate while concurrently removing unbound RBCs. These results also show that the same sample can be used to carry out the multiplexing reaction, i.e., the same sample can be applied to all the spots.

Example 6: Phenotyping of Direct Coombs Positive Red Blood Cells: Direct Antiglobulin Test The objective of this analysis was to identify, by using specific monoclonal or polyclonal antibodies, human IgGs and/or C3d complement fraction adsorbed on in vivo sensitized red blood cells.

Here, to demonstrate the possibility of detecting sensitized red blood cells with the technology of the invention, an anti-human globulin mAb (a murine IgG mAb) was immobilized on the surface of the substrate. The microfluidic probe was used to dispense human IgG sensitized red blood cells and to remove unbound red blood cells. The red color of the red blood cells bound to the specific antibody was then visually detected by camera image capture.
Materials In this example, the binding agent was an anti-human globulin antibody (a murine IgG mAb). The entire surface of a polystyrene slide was manually functionalized with the antibody. The purified antibody was diluted in PBS buffer (pH 7.4) at concentration ranging from 10 to 500 µg/mL and was bound to the surface of the polystyrene slide by passive absorption. After depositing the antibody on the surface of the slide, the slide was saturated by contact with PBS supplemented with 1% BSA to prevent non-specific binding of sample components. These slides were dried and stored at 4° C. until use. The conditions used to obtain an adequate confinement were as follows: channel 1: aspirate, channel 2: dispense, and channel 3: aspirate. Sensitized red blood cells suspensions as well as native red blood cells suspensions were used as samples.
Method To mimic in vivo sensitized red blood cells, human anti-D IgG was used to sensitize red blood cells. D-positive red blood cells that had been washed with 0.9% isotonic saline solution were suspended at 2% in physiologic water. In parallel, a solution of human anti-D mAb at 20 µg/ml was prepared. The washed D-positive RBC solution was mixed with the solution of human anti-D mAb and was incubated for 45 min at 37° C. To remove the unbound antibody, the anti-D sensitized RBCs were washed with 0.9% isotonic saline solution and were suspended at 10%. The anti-D sensitized RBCs were tested in Direct Coombs Cards (IgG+ C3d), and a strong positive reaction was obtained. 2 µl of the sensitized RBC suspension was then aspirated at 1.8 µl/min with channel 2 of the microfluidic probe. The entire surface of the slide was wet with PBS. The probe was then positioned above the slide. After stabilizing the microfluidic probe flow confinement, the microfluidic probe was programmed to follow a straight line along the X-axis at a velocity of 0.02 mm/s.

Anti-D sensitized red blood cells and the same red blood cells without any sensitization (i.e., native RBCs) were deposited with the microfluidic probe on the slide having a binding agent of anti-human globulin antibody. Concurrent with the application of the sample to the binding agent, unbound material was removed by the probe. The presence or absence of red blood cells attached to the antibody was detected by camera image capture. Anti-D sensitized RBCs should bind to the anti-human globulin antibody, whereas RBCs that did not undergo sensitization should not bind to the anti-human globulin antibody.

Figure 15:
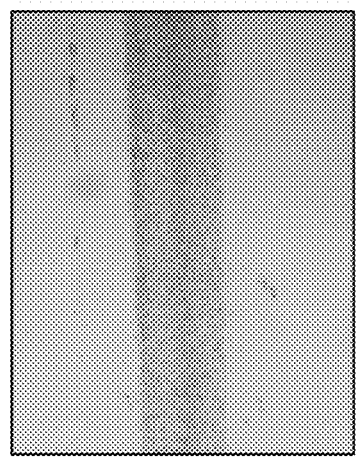
FIG. 15 shows results from direct antiglobulin testing using a microfluidic probe as described in Example 6.

The results show that only the anti-D sensitized red blood cells bound strongly to the anti-human globulin mAb across the entire scanning region (FIG. 15), whereas the native red blood cells did not bind at all (not shown). These results demonstrate that the binding observed is specific. Additionally, these results show that the microfluidic probe can be used in a direct antiglobulin test in which a microfluidic probe is used to apply human IgG sensitized red blood cells to anti-human globulin monoclonal antibodies on a solid substrate while concurrently removing unbound RBCs.

Example 7A: Antibody Screening/Identification

The screening for atypical anti-red blood cell antibodies is required to allow compatible transfusion between a donor and a recipient. The purpose is to verify that the recipient's plasma does not contain antibodies directed against the donor red blood cells which must be transfused. The screening needs to use several red blood cells characterized by the distribution of blood group antigens on their surface. Such screening is as follows: red blood cells whose phenotype is known are incubated with the serum or plasma sample to be tested. If present, specific antibodies bind to the surface of the red blood cells and are detected with a reagent containing an anti-human globulin antibody. By using panels of red blood cells which have or do not have various antigens, it is then possible to determine the specificity of the antibodies present in the sample. To demonstrate the possibility of antibody screening and identification with the technology of the invention, the surface of the substrate was used to immobilize native or hemolyzed phenotyped red blood cells via a universal antibody. The microfluidic probe was then used to dispense anti-D monoclonal antibody to mimic patient plasma. While dispensing anti-D monoclonal antibody, the probe concurrently removed non-specifically bound material. The probe was also used to dispense 10 µg/ml phycoerythrin-labeled anti-human globulin antibody (secondary antibody) to detect bound anti-D monoclonal antibody.

Materials

In this example, the entire surface of polystyrene slides was manually functionalized with an universal anti-red blood cells antibody. The anti-red blood cell antibody used was purified and diluted in PBS buffer (pH 7.4) at concentrations of 100 µg/mL and were bound to the surface of the slides by passive absorption. The slides were then saturated by contact with PBS supplemented with 1% BSA to prevent non-specific binding of sample components. After air drying, the slides were stored at 4° C. until use. Phenotyped red blood cells were washed with 0.9% isotonic saline solution, and then were suspended at 0.5%. This red blood cells suspension was then incubated with a slide during 20 min at 37° C. in a wet room. Then, the slide was washed with a 0.9% isotonic saline solution to remove unbound red blood cells. The microfluidic probe was then used to deposit a sample mixture of 4 µg/ml monoclonal anti-D mAb (primary antibody) and 10 µg/ml phycoerythrin-labeled anti-human globulin mAb (secondary antibody) diluted in a low ionic strength buffer. Because the sample mixture was not detectable without any labeling, the microfluidic probe was run in double flow confinement mode which means that the sample mixture was nested inside another shaped liquid that itself was confined within the immersion liquid (PBS). In this case, the second confinement was carried out with a fluorescein solution, which was visible and guaranteed the appropriate confinement of the sample mixture. With the microfluidic probe, the sample mixture was dispensed with the channel 2 and aspirated with the channel 3, and the fluorescein solution was dispensed with channel 1 and aspirated with channel 4.

Method

The mixture (3 µl) of the monoclonal anti-D mAb with 10 µg/ml phycoerythrin-labeled anti-human globulin mAb was aspirated at 3.5 µl/min with channel 2 of the microfluidic probe. An adequate amount of PBS buffer (processing liquid) was dispensed to wet the whole surface of the slide. The microfluidic probe was then positioned above the slide and the double flow confinement mode was set up. After stabilizing the double flow confinement, the probe was set up to remain between 30 s to 180 s at the same location. Sample application and removal of unbound material was concurrent. The presence or absence of antibody labeled by the anti-human globulin mAb and attached to the native red blood cells was detected by reading the fluorescence with a fluorescence microarray analyzer SensoSpot (Sensovation AG, Radolfzell, GE).

Figure 16:
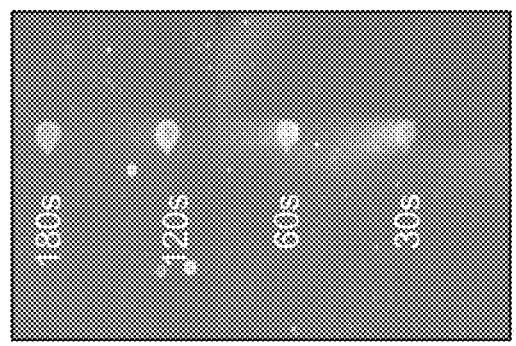
FIG. 16 shows results from antibody screening using a microfluidic probe as described in Example 7A.

As shown in FIG. 16, anti-D mAb bound to the D-positive RBCs no matter how long the probe remained at the same location. Similar results were obtained when the monoclonal anti-D mAb and the labeled anti-human globulin mAb were applied separately to the D-positive RBCs. This experiment demonstrates that the microfluidic probe can be used in an antibody screening/identification method in which sample is applied concurrent with removal of unbound material.

Example 7B: Reverse ABO Grouping Test

The objective of this analysis was to show the presence or absence, in a blood sample, of natural antibodies directed against the A and/or B blood group antigens. The result of this analysis, combined with that obtained in a direct test, will make it possible to establish the ABO group of the sample. The sample used in the reverse ABO grouping test may be a serum, plasma or whole blood sample. To demonstrate the possibility of reverse ABO grouping with the technology of the invention, the surface of the substrate was used to immobilize native phenotyped red blood cells via a universal antibody. For this application, the microfluidic probe was used to deposit patient plasma serum and to remove unbound material.

Materials

As in the previous example, the surface of the entire polystyrene slide was entirely functionalized with an universal anti-red blood cell antibody. After depositing the universal anti-red blood cell antibody onto the surface of the slides, the slides were saturated by contact with PBS supplemented with 1% BSA to prevent non-specific binding of sample. These slides were air dried and were stored at 4° C. until use. Phenotyped A-positive red blood cells were washed with a 0.9% isotonic saline solution and were suspended to a final concentration of 0.5%. This red blood cell suspension was then incubated with a slide for 20 min at 37° C. in a wet room. Next, the slide was washed with a 0.9% isotonic saline solution to remove unbound red blood cells. The microfluidic probe was then used to deposit plasma from a B blood type person. Because the plasma was not detectable without any labeling, the microfluidic probe was again used in double flow confinement mode as in the previous example.

Method

The plasma sample was aspirated at 3.2 µl/min with the channel 2 of the microfluidic probe. An adequate buffer (processing liquid) was dispensed onto the slide to wet the whole surface. The microfluidic probe was positioned above the slide and the double flow confinement mode was then set up. When the double flow confinement was stabilized, the probe was set up to remain between 30 s to 180 s at the same location. Again, application of sample and removal of unbound material occurred simultaneously. The slide was then incubated 15 min at 37° C. in a bath with a 10 µg/ml phycoerythrin-labeled anti-human H+L Ab. The presence or absence of plasma antibody labeled by the anti-human H+L Ab and bound to the native red blood cells was detected by reading the fluorescence with the fluorescence microarray analyzer SensoSpot (Sensovation AG, Radolfzell, GE).

Figure 17:
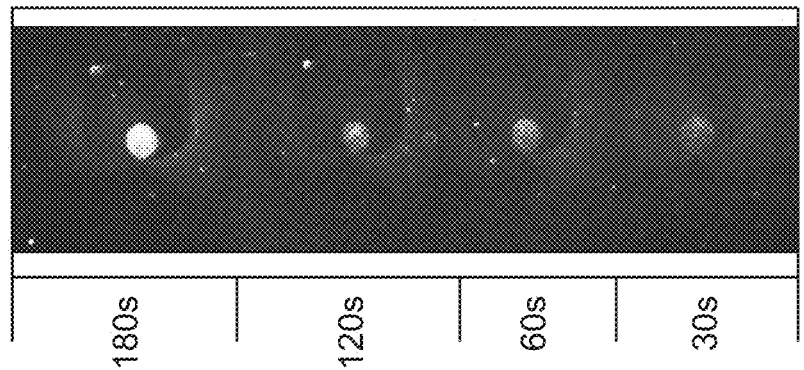
FIG. 17 shows results from reverse ABO grouping using a microfluidic probe as described in Example 7B.

As shown in FIG. 17, anti-D mAb bound to the A-positive RBCs, the intensity of the binding increases with the time where the probe remained at the same location. This experiment demonstrated that a microfluidic probe can be used in a reverse grouping method in which patient plasma is applied to phenotyped red blood cells concurrent with removing unbound plasma material.

Example 8: Cross-Match

One objective of this analysis was to be sure that in the context of a transfusion of one or more blood cell concentrates from donors to a recipient, there was complete donor-recipient compatibility. Another objective was to demonstrate an incompatibility linked to the presence of antibodies in the recipient's plasma, directed against blood group structures carried by the red blood cells of the donor. The microfluidic probe was used to perform the immobilization of donor red blood cells via a universal antibody, to deposit the patient plasma, and to remove non-specifically bound patient plasma material. Detection of the presence or absence of the plasma antibodies bound to the red blood cells was carried out with a labeled anti-human globulin Ab.

Materials

The surface of the entire polystyrene slide was entirely functionalized with an universal anti-red blood cell antibody as in example 7A. After depositing the universal anti-red blood cell antibody on the surface of the slides, the slides were saturated by contact with PBS supplemented with 1% BSA to prevent non-specific binding of sample components. The slides were air dried and were stored at 4° C. until use. A+ donor red blood cells were washed with 0.9% isotonic saline solution and were suspended at a concentration of 50%. To dispense the A+ donor RBCs, the microfluidic probe was operated in hydrodynamic flow confinement mode as follows: channel 1: aspirate, channel 2: dispense, and channel 3: aspirate. Then a double confinement mode was used to dispense A+ or O+ patient plasma as follows: plasma was dispensed with the channel 2 and aspirated with channel 3 and fluorescein solution was dispensed with channel 1 and aspirated with channel 4.

Method

In this example, 2.5 µl of the A+ donor red blood cell suspension (diluted suspension at 50%) was aspirated at 1.5 µl/min with the microfluidic probe. PBS buffer (processing liquid) was dispensed into the slide to wet the whole surface. The microfluidic probe was then positioned above the slide and the flow confinement was then set up. When flow confinement was stabilized, the movement of the microfluidic probe was programmed at 0.03 mm/s to draw a straight line along the X-axis. The length of the line was about 12 mm. During movement of the probe, the A+ donor red blood cells were immediately bound to the universal anti-red blood cell antibody bound to the surface of the slide. Due to the continuous flow, as red blood cells were dispensed, the unbound red blood cells were concurrently removed. The microfluidic probe was then used to deposit the A+ or O+ patient plasma in dual flow confinement mode as previously described. With the microfluidic probe, 2 µl of the plasma was aspirated at 3 µl/min. The microfluidic probe was set up to remain at the same location for 60 seconds with the A+ plasma and for 30 or 60 seconds with the O+ plasma. Concurrent with applying plasma to the previously applied RBCs, unbound material was removed with the probe. The slide was then incubated 15 min at 37° C. in a bath with 10 µg/ml phycoerythrin-labeled anti-human globulin Ab. Finally, the presence or absence of antibody labeled by the phycoerythrin-labeled anti-human globulin Ab and bound to the native red blood cells was detected by reading the fluorescence with the fluorescence microarray analyzer SensoSpot (Sensovation AG, Radolfzell, GE).

Figure 18A:
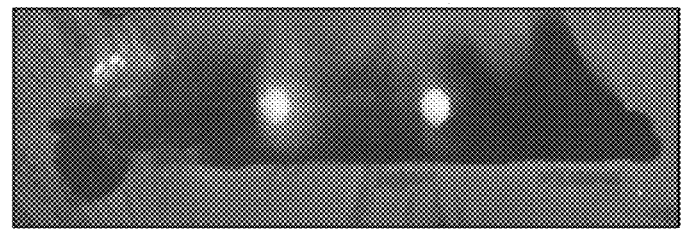
FIGS. 18A-18B show results from cross-matching using a microfluidic probe as described in Example 8.
Figure 18B:
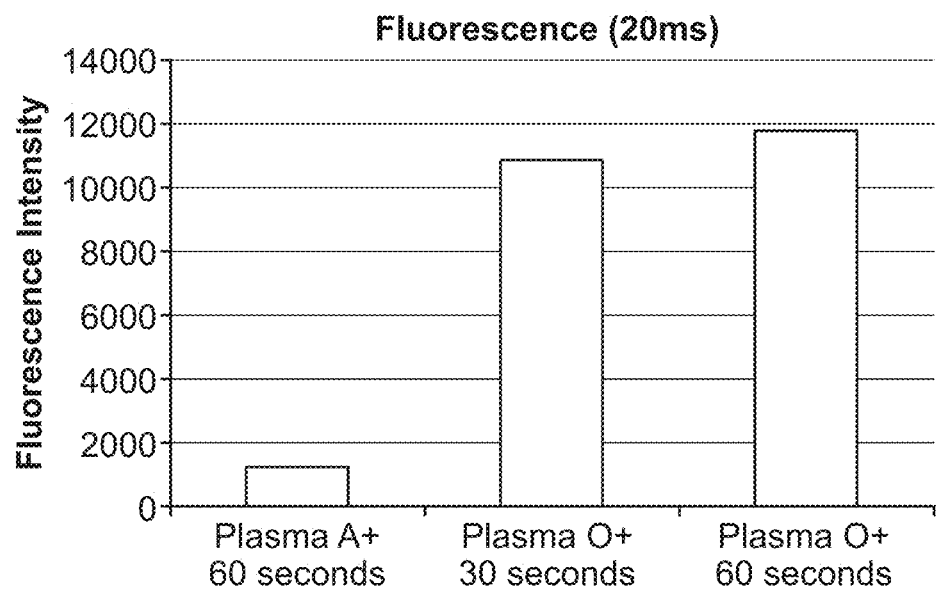

As shown in FIGS. 18A and 18B, the A+ plasma did not bind to the A+ red blood cells (e.g., only a faint spot was detected). However, binding was observed with the O+ plasma, even at an incubation time of 30 seconds. This experiment demonstrated that the microfluidic probe can be used in a cross-matching method in which donor plasma is applied to immobilized red blood cells concurrent with removing unbound plasma material.

As used in this specification and in the claims appended hereto (and in the items herein), the term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

The text of U.S. patent application Ser. No. 13/881,989 is incorporated hereinafter.

We claim:

1. A blood analysis system comprising:
    a substrate having a binding agent immobilized in discreet locations, wherein the binding agent comprises one or more antibodies that bind to: antigens at the surface of red blood cells, antigens on one or more native or hemolyzed phenotyped red blood cells, one or more recombinant blood group antigens, or one or more antibodies to red blood cell antigens;
    a dispenser comprising a plurality of microchannels configured to simultaneously dispense a sample comprising the antigen to which the binding agent binds onto the substrate and to remove the sample from the substrate, the plurality of microchannels comprising microchannels that exclude red blood cells based on size and microchannels sized to allow red blood cells from the sample to flow therethrough;
    a light source configured to illuminate the substrate; and
    a detector configured to detect the presence or absence of red blood cell components bound to the binding agent.

2. The blood analysis system of claim 1, wherein the microchannels that exclude red blood cells have a cross section having a diameter of less than 6 micrometers.

3. The blood analysis of claim 2, wherein the microchannels that exclude red blood cells have a cross section having a diameter of less than 6 micrometers and the microchannels sized to allow red blood cells from a sample to flow therethrough have a diameter of at least 7 micrometers.

4. A blood analysis system for cross-matching comprising:
    a substrate having donor red blood cells immobilized in discreet locations thereon;
    a dispenser configured to simultaneously dispense donor red blood cells or patient plasma onto the substrate and to remove unbound donor red blood cells or unbound components of the patient plasma from the substrate, the dispenser comprising a microfluidic probe having microchannels that exclude red blood cells based on size and microchannels sized to allow red blood cells from a sample to flow therethrough;
    a light source configured to illuminate the substrate; and
    a detector configured to detect the presence or absence of antibodies bound to the donor red blood cells.

5. The blood analysis system of claim 4, wherein the microchannels that exclude red blood cells have a cross section having a diameter of less than 6 micrometers.

6. The blood analysis system of claim 5, wherein the microchannels that exclude red blood cells have a cross section having a diameter of less than 6 micrometers and the microchannels sized to allow red blood cells from a sample to flow therethrough have a diameter of at least 7 micrometers.

* * * * *